US009032635B2

(12) United States Patent  
Herr et al.

(10) Patent No.: US 9,032,635 B2  
(45) Date of Patent: May 19, 2015

(54) PHYSIOLOGICAL MEASUREMENT DEVICE OR WEARABLE DEVICE INTERFACE SIMULATOR AND METHOD OF USE

(71) Applicant: Massachusetts Institute of Technology, Cambridge, MA (US)

(72) Inventors: Hugh M. Herr, Somerville, MA (US); Arthur Petron, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 215 days.

(21) Appl. No.: 13/715,441

(22) Filed: Dec. 14, 2012

(65) Prior Publication Data

US 2013/0197318 A1 Aug. 1, 2013

Related U.S. Application Data

(60) Provisional application No. 61/576,275, filed on Dec. 15, 2011.

(51) Int. Cl.
*A61B 5/107* (2006.01)
*A61B 5/11* (2006.01)
*A61B 5/00* (2006.01)
*A61F 2/76* (2006.01)
(Continued)

(52) U.S. Cl.
CPC ............... *A61B 5/4851* (2013.01); *A61B 5/107* (2013.01); *A61B 5/01* (2013.01); *A61B 5/11* (2013.01); *A61B 5/4848* (2013.01); *A61B 5/1077* (2013.01); *A61B 2562/0247* (2013.01); *A61B 2562/046* (2013.01); *A61F 2/76* (2013.01); *A61F 2002/5049* (2013.01); *A61F 2002/762* (2013.01)

(58) Field of Classification Search
USPC ............. 33/514.2, 555.4, 561.1, 561.2, 561.3
See application file for complete search history.

(56) References Cited

U.S. PATENT DOCUMENTS

| 2,489,291 A | 11/1949 | Henschke et al. |
| 2,529,968 A | 11/1950 | Sartin |
| 3,098,645 A | 7/1963 | Owens |

(Continued)

FOREIGN PATENT DOCUMENTS

| EP | 1393866 | 3/2004 |
| EP | 1408892 | 4/2004 |

(Continued)

OTHER PUBLICATIONS

Herr, Hugh et al. "New Horizons for Orthotic and Prosthetic Technology: Artificial Muscle for Ambulation," The MIT Media Laboratory, pp. 1-9, 2004.

(Continued)

*Primary Examiner* — Christopher Fulton
(74) *Attorney, Agent, or Firm* — Hamilton, Brook, Smith & Reynolds, P.C.

(57) ABSTRACT

A physiological measurement device or wearable device simulator includes a frame and a plurality of surfaces distributed within the frame. For each surface, a surface actuator links the surface of the frame. At least one of: i) force or position imparted by the surface on a physiological feature of a subject by the surface actuator; and ii) the force imparted by the physiological feature of the subject on the surface, can be employed to modulate the positions of the surfaces relative to each other independently of the forces imparted by or on those surfaces, thereby measuring the physiological feature of the subject or simulating a wearable device interface.

34 Claims, 15 Drawing Sheets

(51) Int. Cl.
    *A61B 5/01*        (2006.01)
    *A61F 2/50*        (2006.01)

(56)            References Cited

U.S. PATENT DOCUMENTS

| | | | |
|---|---|---|---|
| 3,207,497 A | 9/1965 | Schoonover | |
| 3,844,279 A | 10/1974 | Konvalin | |
| 4,221,053 A * | 9/1980 | Bobel et al. | 33/552 |
| 4,442,390 A | 4/1984 | Davis | |
| 4,463,291 A | 7/1984 | Usry | |
| 4,518,307 A | 5/1985 | Bloch | |
| 4,532,462 A | 7/1985 | Washbourn et al. | |
| 4,546,295 A | 10/1985 | Wickham et al. | |
| 4,546,296 A | 10/1985 | Washbourn et al. | |
| 4,546,297 A | 10/1985 | Washbourn et al. | |
| 4,546,298 A | 10/1985 | Wickham et al. | |
| 4,569,352 A | 2/1986 | Petrofsky et al. | |
| 4,600,357 A | 7/1986 | Coules | |
| 4,657,470 A | 4/1987 | Clarke et al. | |
| 4,843,921 A | 7/1989 | Kremer | |
| 4,865,376 A | 9/1989 | Leaver et al. | |
| 4,872,803 A | 10/1989 | Asakawa | |
| 4,909,535 A | 3/1990 | Clark et al. | |
| 4,921,293 A | 5/1990 | Ruoff et al. | |
| 4,921,393 A | 5/1990 | Andeen et al. | |
| 4,923,474 A | 5/1990 | Klasson et al. | |
| 4,923,475 A | 5/1990 | Gosthnian et al. | |
| 4,936,295 A | 6/1990 | Crane | |
| 4,964,402 A | 10/1990 | Grim et al. | |
| 4,989,161 A | 1/1991 | Oaki | |
| 4,998,354 A * | 3/1991 | Silverman et al. | 33/514.2 |
| 5,009,512 A * | 4/1991 | Lessi et al. | 374/6 |
| 5,012,591 A | 5/1991 | Asakawa | |
| 5,049,797 A | 9/1991 | Phillips | |
| 5,062,673 A | 11/1991 | Mimura | |
| 5,088,478 A | 2/1992 | Grim | |
| 5,092,902 A | 3/1992 | Adams et al. | |
| 5,112,296 A | 5/1992 | Beard et al. | |
| 5,174,168 A | 12/1992 | Takagi et al. | |
| 5,181,933 A | 1/1993 | Phillips | |
| 5,252,102 A | 10/1993 | Singer et al. | |
| 5,294,873 A | 3/1994 | Seraji | |
| RE34,661 E | 7/1994 | Grim | |
| 5,327,790 A | 7/1994 | Levin et al. | |
| 5,367,790 A | 11/1994 | Gamow et al. | |
| 5,383,939 A | 1/1995 | James | |
| 5,405,409 A | 4/1995 | Knoth | |
| 5,442,270 A | 8/1995 | Tetsuaki | |
| 5,443,521 A | 8/1995 | Knoth et al. | |
| 5,456,341 A | 10/1995 | Garnjost et al. | |
| 5,458,143 A | 10/1995 | Herr | |
| 5,476,441 A | 12/1995 | Durfee et al. | |
| 5,502,363 A | 3/1996 | Tasch et al. | |
| 5,514,185 A | 5/1996 | Phillips | |
| 5,556,422 A | 9/1996 | Powell, III et al. | |
| 5,571,205 A | 11/1996 | James | |
| 5,640,779 A * | 6/1997 | Rolloff et al. | 33/514.2 |
| 5,643,332 A | 7/1997 | Stein | |
| 5,650,704 A | 7/1997 | Pratt et al. | |
| 5,662,693 A | 9/1997 | Johnson et al. | |
| 5,701,686 A | 12/1997 | Herr et al. | |
| 5,718,925 A | 2/1998 | Kristinsson et al. | |
| 5,748,845 A | 5/1998 | Labun et al. | |
| 5,776,205 A | 7/1998 | Phillips | |
| 5,885,809 A | 3/1999 | Effenberger et al. | |
| 5,888,212 A | 3/1999 | Petrofsky et al. | |
| 5,888,213 A | 3/1999 | Sears et al. | |
| 5,898,948 A | 5/1999 | Kelly et al. | |
| 5,910,720 A | 6/1999 | Williamson et al. | |
| 5,932,230 A | 8/1999 | DeGrate | |
| 5,944,760 A | 8/1999 | Christensen | |
| 5,971,729 A | 10/1999 | Kristinsson et al. | |
| 5,972,036 A | 10/1999 | Kristinsson et al. | |
| 5,980,435 A | 11/1999 | Joutras et al. | |
| 6,029,374 A | 2/2000 | Herr et al. | |
| 6,056,712 A | 5/2000 | Grim | |
| 6,067,892 A | 5/2000 | Erickson | |
| 6,071,313 A | 6/2000 | Phillips | |
| 6,136,039 A | 10/2000 | Kristinsson et al. | |
| 6,144,385 A | 11/2000 | Girard | |
| 6,160,264 A * | 12/2000 | Rebiere | 250/559.22 |
| 6,202,806 B1 | 3/2001 | Sandrin et al. | |
| 6,223,648 B1 | 5/2001 | Erickson | |
| 6,240,797 B1 | 6/2001 | Morishima et al. | |
| 6,267,742 B1 | 7/2001 | Krivosha et al. | |
| 6,415,199 B1 * | 7/2002 | Liebermann | 700/132 |
| 6,416,703 B1 | 7/2002 | Kristinsson et al. | |
| 6,430,831 B1 * | 8/2002 | Sundman | 33/515 |
| 6,443,993 B1 | 9/2002 | Koniuk | |
| 6,456,884 B1 | 9/2002 | Kenney | |
| 6,478,826 B1 | 11/2002 | Phillips et al. | |
| 6,485,776 B2 | 11/2002 | Janusson et al. | |
| 6,493,958 B1 * | 12/2002 | Tadin | 33/515 |
| 6,507,757 B1 | 1/2003 | Swain et al. | |
| 6,511,512 B2 | 1/2003 | Phillips et al. | |
| 6,517,503 B1 | 2/2003 | Naft et al. | |
| 6,585,774 B2 | 7/2003 | Dean, Jr. et al. | |
| 6,589,289 B2 | 7/2003 | Ingimarsson | |
| 6,592,539 B1 | 7/2003 | Einarsson et al. | |
| 6,610,101 B2 | 8/2003 | Herr et al. | |
| 6,626,952 B2 | 9/2003 | Janusson et al. | |
| 6,660,042 B1 | 12/2003 | Curcie et al. | |
| 6,666,796 B1 | 12/2003 | MacCready | |
| 6,706,364 B2 | 3/2004 | Janusson et al. | |
| 6,752,774 B2 | 6/2004 | Townsend et al. | |
| 6,764,520 B2 | 7/2004 | Deffenbaugh et al. | |
| 6,811,571 B1 | 11/2004 | Phillips | |
| D503,480 S | 3/2005 | Ingimundarson et al. | |
| D503,802 S | 4/2005 | Bjarnason | |
| 6,887,279 B2 | 5/2005 | Phillips et al. | |
| 6,907,672 B2 * | 6/2005 | Said | 33/552 |
| 6,923,834 B2 | 8/2005 | Karason | |
| 6,936,073 B2 | 8/2005 | Karason | |
| 6,942,629 B2 | 9/2005 | Hepburn et al. | |
| 6,945,947 B2 | 9/2005 | Ingimundarson et al. | |
| 6,966,882 B2 | 11/2005 | Horst | |
| 6,969,408 B2 | 11/2005 | Lecomte et al. | |
| 7,001,563 B2 | 2/2006 | Janusson et al. | |
| 7,025,793 B2 | 4/2006 | Egilsson | |
| 7,029,500 B2 | 4/2006 | Martin | |
| 7,037,283 B2 | 5/2006 | Karason et al. | |
| D523,149 S | 6/2006 | Bjarnason | |
| 7,063,727 B2 | 6/2006 | Phillips et al. | |
| 7,077,818 B2 | 7/2006 | Ingimundarson et al. | |
| 7,094,058 B2 | 8/2006 | Einarsson | |
| 7,094,212 B2 | 8/2006 | Karason et al. | |
| D527,825 S | 9/2006 | Ingimundarson et al. | |
| D529,180 S | 9/2006 | Ingimundarson et al. | |
| 7,101,487 B2 | 9/2006 | Hsu et al. | |
| 7,105,122 B2 | 9/2006 | Karason | |
| 7,107,180 B2 | 9/2006 | Karason | |
| 7,118,601 B2 | 10/2006 | Yasui et al. | |
| 7,118,602 B2 | 10/2006 | Bjarnason | |
| 7,136,722 B2 | 11/2006 | Nakamura et al. | |
| D533,280 S | 12/2006 | Wyatt et al. | |
| 7,144,429 B2 | 12/2006 | Carstens | |
| 7,145,305 B2 | 12/2006 | Takenaka et al. | |
| 7,154,017 B2 | 12/2006 | Sigurjonsson et al. | |
| 7,161,056 B2 | 1/2007 | Gudnason et al. | |
| 7,169,188 B2 | 1/2007 | Carstens | |
| 7,169,189 B2 | 1/2007 | Bjarnason et al. | |
| 7,169,190 B2 | 1/2007 | Phillips et al. | |
| 7,198,071 B2 | 4/2007 | Bisbee et al. | |
| 7,198,610 B2 | 4/2007 | Ingimundarson et al. | |
| 7,217,060 B2 | 5/2007 | Ingimarsson | |
| 7,220,889 B2 | 5/2007 | Sigurjonsson et al. | |
| 7,223,899 B2 | 5/2007 | Sigurjonsson | |
| 7,225,554 B2 * | 6/2007 | Madsen | 33/512 |
| 7,227,050 B2 | 6/2007 | Sigurjonsson et al. | |
| 7,230,154 B2 | 6/2007 | Sigurjonsson | |
| 7,235,108 B2 | 6/2007 | Carstens | |
| 7,240,876 B2 | 7/2007 | Doubleday et al. | |
| 7,266,910 B2 | 9/2007 | Ingimundarson | |
| 7,270,644 B2 | 9/2007 | Ingimundarson | |

(56) References Cited

U.S. PATENT DOCUMENTS

| | | | |
|---|---|---|---|
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,318,286 B1 * | 1/2008 | Willette et al. ............. 33/561.1 |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,770,842 B2 | 8/2010 | Benson |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2002/0170193 A1 * | 11/2002 | Townsend et al. ............. 33/512 |
| 2003/0093021 A1 | 5/2003 | Goffer |
| 2003/0125814 A1 | 7/2003 | Paasivaara et al. |
| 2003/0139783 A1 | 7/2003 | Kilgore et al. |

(56) References Cited

U.S. PATENT DOCUMENTS

| | | | |
|---|---|---|---|
| 2003/0163206 | A1 | 8/2003 | Yasui et al. |
| 2003/0195439 | A1 | 10/2003 | Caselnova |
| 2004/0039454 | A1 | 2/2004 | Herr et al. |
| 2004/0049290 | A1 | 3/2004 | Bedard |
| 2004/0054423 | A1 | 3/2004 | Martin |
| 2004/0064195 | A1 | 4/2004 | Herr |
| 2004/0088025 | A1 | 5/2004 | Gesotti |
| 2004/0181118 | A1 | 9/2004 | Kochamba |
| 2004/0181289 | A1 | 9/2004 | Bedard et al. |
| 2005/0007834 | A1 | 1/2005 | Hidaka |
| 2005/0043614 | A1 | 2/2005 | Huizenga et al. |
| 2005/0049652 | A1 | 3/2005 | Tong |
| 2005/0059908 | A1 | 3/2005 | Bogert |
| 2005/0085948 | A1 | 4/2005 | Herr et al. |
| 2005/0155444 | A1 | 7/2005 | Otaki et al. |
| 2005/0209707 | A1 | 9/2005 | Phillips et al. |
| 2005/0228515 | A1 | 10/2005 | Musallam et al. |
| 2006/0004307 | A1 | 1/2006 | Horst |
| 2006/0064047 | A1 | 3/2006 | Shimada et al. |
| 2006/0069448 | A1 | 3/2006 | Yasui |
| 2006/0094989 | A1 | 5/2006 | Scott et al. |
| 2006/0185183 | A1* | 8/2006 | Stieglitz et al. ............... 33/555.4 |
| 2006/0213305 | A1 | 9/2006 | Sugar et al. |
| 2006/0224246 | A1 | 10/2006 | Clausen et al. |
| 2006/0249315 | A1 | 11/2006 | Herr et al. |
| 2006/0258967 | A1 | 11/2006 | Fujil et al. |
| 2006/0264790 | A1 | 11/2006 | Kruijsen et al. |
| 2006/0276728 | A1 | 12/2006 | Ashihara et al. |
| 2007/0016329 | A1 | 1/2007 | Herr et al. |
| 2007/0043449 | A1 | 2/2007 | Herr et al. |
| 2007/0050044 | A1 | 3/2007 | Haynes et al. |
| 2007/0123997 | A1 | 5/2007 | Herr et al. |
| 2007/0129653 | A1 | 6/2007 | Sugar et al. |
| 2007/0162152 | A1 | 7/2007 | Herr et al. |
| 2007/0267791 | A1 | 11/2007 | Hollander et al. |
| 2008/0114272 | A1 | 5/2008 | Herr et al. |
| 2008/0155444 | A1 | 6/2008 | Pannese et al. |
| 2009/0030530 | A1 | 1/2009 | Martin |
| 2009/0222105 | A1 | 9/2009 | Clausen |
| 2011/0224804 | A1 | 9/2011 | Clausen et al. |
| 2011/0245931 | A1 | 10/2011 | Clausen et al. |
| 2011/0260380 | A1 | 10/2011 | Hollander et al. |
| 2011/0278857 | A1 | 11/2011 | Sugar et al. |
| 2012/0271433 | A1 | 10/2012 | Galea et al. |

FOREIGN PATENT DOCUMENTS

| | | |
|---|---|---|
| EP | 1534117 | 6/2005 |
| WO | WO 03/009787 A2 | 2/2003 |
| WO | WO 03/068453 | 8/2003 |
| WO | WO 2004/016158 A2 | 2/2004 |
| WO | WO 2004/017872 A1 | 3/2004 |
| WO | WO 2004/019832 A1 | 3/2004 |
| WO | WO 2010/027968 A2 | 3/2010 |

OTHER PUBLICATIONS

Williamson, Matthew M., "Series Elastic Actuators," MIT Artificial Intelligence Laboratory, Jan. 1995.

Au, S.K. et al., "Powered Ankle-Foot Prosthesis for the Improvement of Amputee Ambulation," paper presented at the Proceedings of the 29th Annual International Conference of the IEEE Eng. Med. Bio. Soc., Cité Internationale, Lyon, France, (Aug. 2007).

International Search Report and Written Opinion for corresponding International Application No. PCT/US2010/022783, Dated: May 4, 2010.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A. et al., "Active Ankle Foot Orthoses (AAFO)," Retrieved from: http://www.ai,mit.edu. Artificial Intelligence Laboratory, Massachusetts Institute of Technology, Cambridge, Massachusetts, 3 pages.

Dollar, et al., "Lower Extremity Exoskeletions and Active Orthoses: Challenges and State-of-the-Art," *IEEE Transcations on Robotics*, vol. 24, No. 1, Feb. 2008, 15 pages.

Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.

Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).

Hogan, N., "Impedance Control: An Approach to Manipulation: Part II—Implementation," *Journal of Dynamic Systems, Measurement and Control*, 107: 8-16 (1985).

Hogan, N., "Impedance Control: An Approach to Manipulation: Part III—Application," *Journal of Dynamics Systems, Measurement and Control*. 107: 17-24 (1985).

Kim, J.-H. et al., "Realization of Dynamic Walking for the Humaniod Robot Platform KHR-1," *Advanced Robotics*, 18(7): 749-768, (2004).

Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).

Klute, G.K. et al., "Artificial Muscles: Actuators for Biorobotic Systems," *The International Journal of Robotics Research*, 21(4): 295-309 (2002).

Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.

Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al., "Intelligent Transtibial Prostheses with Muscle-Like Actuators," 2002 American Physiological Society Intersociety Meeting: The Power of Comparative Physiology: Evolution, Integration, and Applied, 1 page.

Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).

Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.

Klute, G.K. et al., "Variable Stiffness Prosthesis for Transtibial Amputees," Dept of Veteran Affairs, Seattle, WA USA, 2 pages.

International Search Report and Written Opinion for International Application No. PCT/US2009/055600, Mailed: Apr. 29, 2010 (23 pages).

International Search Report and Written Opinion for International Application No. PCT/US2010/047279, Mailed: Jan. 19, 2011 (11 pages).

International Search Report and Written Opinion for International Application No. PCT/US2011/031105, Mailed: Oct. 11, 2011 (16 pages).

J. Hitt et al., "The Sparky (Spring Ankle with Regenerative Kinetics) Projects: Design and Analysis of a Robotic Transtibial prosthesis with Regenerative Kinetics," in Proc. IEEE Int. Conf. Robot. Autom., Orlando, Fla., pp. 2939-2945, May 2006.

Sup, F. et al., "Design and Control of a Powered Transfemoral Prosthesis," *The International Journal of Robotics Research*, vol. 27, No. 2, pp. 263-273 (2008).

Geyer, H. et al., "A Muscle-Reflex Model That Encodes Principles of Legged Mechanics Predicts Human Walking Dynamics and Muscle

(56) References Cited

OTHER PUBLICATIONS

Activities," *IEEE Transactions on Neural Systems and Rehabilitation Engineering*, vol. 18, No. 3, pp. 263-273 (Jun. 2010).
Geyer, H. et al., "Positive Force Feedback in Bouncing Gaits?," *Proc. R Society. Lond. B*, 270, pp. 2173-2183 (2003).
Abbas, J.J. et al., "Neural Network Control of Functional Neuromuscular Stimulation Systems: Computer Simulation Studies," *IEEE Transactions on Biomedical Engineering*, vol. 42, No. 11, Nov. 1995, pp. 1117-1127.
Abul-Haj, C.J. et al., "Functional Assessment of Control Systems for Cybernetic Elbow Prostheses-Part II: Application of the Technique," *IEEE Transactions on Biomedical Engineering*, vol. 17, No. 11, Nov. 1990, pp. 1037-1047.
Akazawa, K. et al., "Biomimetic EMG-Prosthesis-Hand, $18^{th}$ Annual International Conference of the IEEE Engineering in Medicine and Biology Society," Amsterdam 1996, pp. 535 and 536.
Aminian, K. et al., "Estimation of Speed and Incline of Walking Using Neural Network," *IEEE Transactions of Instrumentation and Measurement*, 44(3): 743-746 (1995).
Anderson, F.C. et al., "Dynamic Optimization of Human Walking," *Journal of Biomechanical Engineering*, 123: 381-390 (2001).
Andrews, B.J. et al., "Hybrid FES Orthosis Incorporating Closed Loop Control and Sensory Feedback," *J. Biomed. Eng.*, 10: 189-195(1988).
Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.
Au, S.K. et al., "Biomechanical Design of a Powered Ankle-Foot Prosthesis," Proceedings of the 2007 IEEE $10^{th}$ International Conference on Rehabilitation Robotics, Noordwijk, The Netherlands, Jun. 12-15, pp. 298-303.
Au, S.K. et al., "An EMG-Position Controlled System for an Active Ankle-Foot Prosthesis: An Initial Experimental Study," Proceedings of the 2005 IEEE $9^{th}$ International Conference on Rehabilitation Robotics, Chicago, IL., pp. 375-379.
Au, S.K. et al., "Initial Experimental Study on Dynamic Interaction Between an Amputee and a Powered Ankle-Foot Prostheses," Harvard-MIT Division of Health Sciences and Technology, MIT, Cambridge, MA.
Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.
Au, S.K. et al., "Powered Ankle—Foot Prosthesis Improves Walking Metabolic Economy," *IEEE Transactions on Robotics*, 25(1): 51-66 (2009).
Au, S.K. et al., "Powered Ankle—Foot Prosthesis for the Improvement of Amputee Ambulation," paper presented at the Proceedings of the $29^{th}$ Annual International Conference of the IEEE EMBS Cité Internationale, Lyon, France, (Aug. 2007).
Au, S. et al., "Powered Ankle-Foot Prosthesis to Assist Level-Ground and Stair-Descent Gaits," *Neural Networks*, 21: 654-666 (2008).
Barth, D.G. et al., "Gait Analysis and Energy Cost of Below-Knee Amputees Wearing Six Different Prosthetic Feet," *JPO*, 4(2): 63 (1992).
Bateni, H. et al., "Kinematic and Kinetic Variations of Below-Knee Amputee Gait," *JPO*, 14(1):1-12 (2002).
Baten, Chris T.M. et al., "Inertial Sensing in Ambulatory Back Load Estimation," paper presented at the $18^{th}$ Annual International Conference of the IEEE Engineering in Medicine and Biology Society, Amsterdam, 1996, pp. 497-498.
Blaya, J. et al., "Active Ankle Foot Orthoses (AAFO)," Artificial Intelligence Laboratory, Massachusetts Institute of Technology, Cambridge, MA, pp. 275-277.
Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).

Blaya, J.A. et al., "Force-Controllable Ankle-Foot Orthosis (AFO) to Assist Drop Foot Gait," Massachusetts Institute of Technology, Feb. 2003, pp. 1-96.
Blickhan, R., "The Spring-Mass Model for Running and Hopping," *J. Biomechanics*, 22(11 /12): 1217-1227 (1989).
Bortz, J.E. "A New Mathematical Formulation for Strapdown Inertial Navigation," *IEEE Transactions on Aerospace and Electronic Systems*, AES-7(1): 61-66 (1971).
Bouten, C.V. et al., "Assessment of Energy Expenditure for Physical Activity Using a Triaxial Accelerometer," *Medicine and Science in Sports and Exercise*, pp. 1516-1523.
Brockway, J.M., "Derivation of Formulae Used to Calculate Energy Expenditure in Man," *Human Nutrition: Clinical Nutrition* (1987), 41C, pp. 463-471.
Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46.
AJG The American Journal of Gastroenterology, "Symptoms Diagnosis," 105(4): 1-875 (2010).
Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.
American Journal of Physical Medicine & Rehabilitation, 71(5): 1-278 (1992).
Colgate, James Edward, "The Control of Dynamically Interacting Systems," Massachusetts Institute of Technology, Aug. 1988, pp. 1-15.
Collins, S.H. et al., "Controlled Energy Storage and Return Prosthesis Reduces Metabolic Cost of Walking," ISB XXth Congress-ASB $29^{th}$ Annual Meeting, Jul. 31-Aug. 5, Cleveland, Ohio, pp. 804.
Collins, S.H. et al., "Efficient Bipedal Robots Based on Passive-Dynamic Walkers," Feb. 11, 2005, pp. 1-8.
Crago, P.E. et al., "New Control Strategies for Neuroprosthetic Systems," *Journal of Rehabilitation Research and Development*, vol. 33, No. 2, Apr. 1996, pp. 158-172.
Daley, M.A. et al., "Running Stability is Enhanced by a Proximo-Distal Gradient in Joint Neuromechanical Control," *The Journal of Experimental Biology*, vol. 210, pp. 383-394 (Feb. 2007).
Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).
Dietz, V. "Proprioception and Locomotor Disorders," *Nature Reviews*, vol. 3, pp. 781-790 (Oct. 2002).
Dietz, V. "Spinal Cord Pattern Generators for Locomotion," *Clinical Neurophysiology*, vol. 114, Issue 8, pp. 1-12 (Aug. 2003).
Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.
Doke, J. et al., "Mechanics and Energetics of Swinging the Human Leg," *The Journal of Experimental Biology*, vol. 208, pp. 439-445 (2005).
Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.
Donelan, J.M. et al., "Force Regulation of Ankle Extensor Muscle Activity in Freely Walking Cats," *Journal of Neurophysiology*, vol. 101, pp. 360-371 (2009).
Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).
Donelan, J.M. et al., "Simultaneous Positive and Negative External Mechanical Work in Human Walking," *Journal of Biomechanics*, vol. 35, 2002, pp. 117-124 (2002).
HemiHelp, "Ankle & Foot Splints or Orthoses," (AFOs).
HemiHelp, "Foot & Ankle Splints or Orthoses," pp. 1-5.
Drake, C., "Foot & Ankle Splints or Orthoses," pp. 1-3.
Eilenberg, M.F. "A Neuromuscular-Model Based Control Strategy for Powered Ankle-Foot Prostheses," Massachusetts Institute of Technology, pp. 1-90.

(56) References Cited

OTHER PUBLICATIONS

Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).

Ekeberg, Ö et al., "Simulations of Neuromuscular Control in Lamprey Swimming," The Royal Society, *Phil. Trans. R. Soc. Land*, vol. 354, pp. 895-902 (1999).

Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.

Eppinger, S.D. et al., "Three Dynamic Problems in Robot Force Control," *IEEE Transactions on Robotics and Automation*, vol. 8, No. 6, pp. 772-778 (Dec. 1992).

Esquenazi, A. et al., "Rehabilitation After Amputation," vol. 91, No. 1, pp. 1-22 (Jan. 2001).

Farley, C.T. et al., "Energetics of Walking and Running: Insights From Simulated Reduced-Gravity Experiments," Harvard University, pp. 2709-2712.

Farry, K.A. et al., "Myoelectric Teleoperation of a Complex Robotic Hand," *IEEE Transactions on Robotics and Automation*, vol. 12, No. 5, pp. 775-778 (Oct. 1996).

Featherstone, R., "Robot Dynamics Algorithms," Edinburgh University, pp. 1-173.

Fite, K. et al., "Design and Control of an Electrically Powered Knee Prosthesis," Proceedings of the 2007 IEEE 10$^{th}$ International Conference on Rehabilitation Robotics, Jun. 12-15, The Netherlands, pp. 902-905.

Flowers, W.C., "A Man-Interactive Simulator System for Above-Knee Prosthetics Studies," MIT, pp. 1-94.

Fod, A. et al., "Automated Derivation of Primitives for Movement Classification," *Autonomous Robots*, vol. 12, No. 1, pp. 39-54 (Jan. 2002).

Frigon, A. et al., "Experiments and Models of Sensorimotor Interactions During Locomotion," *Biological Cybernetics*, vol. 95, pp. 606-627 (2006).

Fujita et al., "Joint Angle Control with Command Filter for Human Ankle Movement Using Functional Electrical Stimulation," IEEE Ninth Annual Conference of the Engineering in Medicine and Biology Society.

Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).

Gates, D.H. Thesis: "Characterizing Ankle Function During Stair Ascent, Descent, and Level Walking for Ankle Prosthesis and Orthosis Design," Boston University, pp. 1-84.

Gerritsen, K.G.M. et al., "Direct Dynamics Simulation of the Impact Phase in Heel-Toe Running," *J. Biomechanics*, vol. 28, No. 6, pp. 661-668 (1995).

Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10 (Date not provided).

Geyer, H. et al., "Compliant Leg Behavior Explains Basic Dynamics of Walking and Running," *Proc. R. Soc. B*, vol. 273, pp. 2861-2867 (2006).

Geyer, H. et al., "Positive Force Feedback in Bouncing Gaits?," *Proc. R. Soc. Lond, B*, vol. 270, pp. 2173-2183 (2003).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," University of Calgary, Canada, pp. 1-14.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).

Gregoire, L. et al., "Role of Mono- and Biarticular Muscles in Explosive Movements," *International Journal of Sports Medicine*, vol. 5, No. 6, pp. 299-352 (Dec. 1984).

Grillner, S. and Zangger, P., "On the Central Generation of Locomotion in the Low Spinal Cat," *Experimental Brain Research*, 34: 241-261 (1979).

Grimes, D.L., "An Active Multi-Mode Above-Knee Prosthesis Controller," unpublished doctoral dissertation, Massachusetts Institute of Technology (1979).

Gunther, M. et al., "Human Leg Design: Optimal Axial Alignment Under Constraints," *J. Math. Biol.*, 48: 623-646 (2004).

Günther, M., and Ruder, H., "Synthesis of Two-Dimensional Human Walking: a test of the λ-model," *Biol. Cybern.*, 89: 89-106 (2003).

Gu, W.J., "The Regulation of Angular Momentum During Human Walking," unpublished doctoral dissertation, Massachusetts Institute of Technology (2003).

Brady, M. et al., "Robot Motion: Planning and Control," The MIT Press, Cambridge (1982).

Hansen, A.H., et al., "The Human Ankle During Walking: Implications for Design of Biomimetic Ankle Prostheses," *Journal of Biomechanics*, 37: 1467-1474 (2004).

Hayes, W.C., et al., "Leg Motion Analysis During Gait by Multiaxial Accelerometry: Theoretical Foundations and Preliminary Validations," *Journal of Biomechanical Engineering*, 105: 283-289 (1983).

Heglund, N. et al., "A Simple Design for a Force-Plate to Measure Ground Reaction Forces," *J. Exp. Biol.*, 93: 333-338 (1981).

Herr, H.M. et al., "A Model of Scale Effects in mammalian Quadrupedal Running," *The Journal of Experimental Biology*, 205: 959-967 (2002).

Herr, H.M., and Popovic, M., "Angular Momentum in Human Walking," *The Journal of Experimental Biology*, 211: 467-481 (2008).

Herr, H.M., and McMahon, T.A., "A Trotting Horse Model," *The International Journal of Robotics Research*, 19: 566-581 (2000).

Herr, H.M., and Wilkenfeld, A., "User-adaptive Control of a Magnetorheological Prosthetic Knee," *Industrial Robot: An International Journal*, 30(1): 42-55 (2003).

Heyn, A., et al., "The Kinematics of the Swing Phase Obtained From Accelerometer and Gyroscope Measurements," paper presented at the 18$^{th}$ Annual International Conference of the IEEE Engineering in Medicine and Biology Society, Amsterdam (1996).

Hill, A.V., "The Heat of Shortening and the Dynamic Constants of Muscle," *Proc. R. Soc. Lond.*, 126: 136-195 (1938).

Hirai, K., et al., "The Development of Honda Humanoid Robot," paper presented at the 1998 IEEE International Conference on Robotics & Automation (1998).

Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada (2007).

Hofbaur, M.W., et al., "Hybrid Diagnosis with Unknown Behavioral Modes," Proceedings of the 13$^{th}$ International Workshop on Principles of Diagnosis (DX02) (2002).

Hofbaur, M.W., and Williams, B.C., "Mode Estimation of Probabilistic Hybrid Systems," MIT Space Systems and Artificial Intelligence Laboratories and Graz University of Technology, Department of Automatic Control.

Hof, A.L., et al., "Calf Muscle Moment, Work and Efficiency in Level Walking: Role of Series Elasticity," *J. Biochem.*, 16: 523-537 (1983).

Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).

(56) References Cited

OTHER PUBLICATIONS

Hofmann, A.G., "Robust Execution of Bipedal Walking Tasks From Biomechanical Principles," unpublished doctoral dissertation for Massachusetts Institute of Technology (2006).

Hogan, N., "A Review of the Methods of Processing EMG for Use As a Proportional Control Signal," *Biomedical Engineering*, 11(3): 81-86 (1976).

Hogan, N., "Impedance Control-An Approach to Manipulation," unpublished doctoral dissertation for Department of Mechanical Engineering and Laboratory of Manufacturing and Productivity, Massachusetts Institute of Technology, pp. 304-313.

Hogan, N., and Buerger, S.P., "Impedance and Interaction Control, Robots and Automation Handbook."

Hogan, N., "Impedance Control: An Approach to Manipulation, Part III—Applications," *Journal of Dynamic Systems, Measurement, and Control*, 107: 17-24 (1985).

Hogan, N., "Impedance Control: An Approach to Manipulation: Part II—Implementation," *Journal of Dynamic Systems, Measurement, and Control*, 107: 8-16 (1985).

Hogan, N., "Impedance Control: An Approach to Manipulation: Part I—Theory," *Journal of Dynamic Systems, Measurement, and Control*, 107: 1-7 (1985).

Hollander, K.W. et al., "Adjustable Robotic Tendon using a 'Jack Spring'™," Proceedings of the 2005 IEEE, $9^{th}$ International Conference on Rehabilitation Robotics, Jun. 28-Jul. 1, 2005, Chicago, IL, USA, pp. 113-118.

Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.

Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).

Huang, Q. et al., "Planning Walking Patterns for a Biped Robot," *IEEE Transactions on Robotics and Automation*,17(3): 280-289 (Jun. 2001).

Hultborn, H., "Spinal reflexes, mechanisms and concepts: From Eccles to Lundberg and beyond," *Progress in Neurobiology*,78: 215-232 (2006).

Ijspeert, A.J., "Central pattern generators for locomotion control in animals and robots: a review," *Preprint of Neural Networks*, vol. 21, No. 4, pp. 642-653 (2008).

Ijspeert, A.J. et al., "From swimming to walking with a salamander robot driven by a spinal cord model," pp. 1-5.

Ivashko, D.G. et al., "Modeling the spinal cord neural circuitry controlling cat hindlimb movement during locomotion," *Neurocomputing*, 52-54, pp. 621-629 (2003).

International Search Report and Written Opinion for International Application No. PCT/US2009/055600, Mailed: Apr. 29, 2010.

International Preliminary Report on Patentability for International Application No. PCT/US2010/047279; Mailed: Mar. 15, 2012.

International Search Report and Written Opinion for International Application No. PCT/US2010/047279; Mailed: Jan. 19, 2011.

International Search Report and Written Opinion for International Application No. PCT/US2011/031105, Mailed: Oct. 11, 2011.

Johansson, J.L. et al., "A Clinical Comparison of Variable-Damping and Mechanically Passive Prosthetic Knee Devices," Variable-Damping vs. Mechanically Passive Prosthetic Knees, Aug. 2005.

Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).

Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).

Kadaba, M.P. et al., "Measurement of Lower Extremity Kinematics During Level Walking," *Journal of Orthapedic Research*, pp. 383-392, 1990.

Kadaba, M.P. et al., "Repeatability of Kinematic, Kinetic, and Electromyographic Data in Normal Adult Gait," *Journal of Orthapedic Research*, pp. 849-860, 1989.

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2," Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katie, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. et al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

Khatib, O. et al., "Whole-Body Dynamic Behavior and Control of Human-Like Robots," *International Journal of Humanoid Robotics*, vol. 1, No. 1, pp. 29-43 (2004).

Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).

Kim, J.-H. et al., "Realization of dynamic walking for the humanoid robot platform KHR-1," *Advanced Robotics*, vol. 18, No. 7, pp. 749-768 (2004).

Kirkwood, C.A. et al., "Automatic detection of gait events: a case study using inductive learning techniques," *J. Biomed. Eng.*, vol. 11, pp. 511-516 (Nov. 1989).

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.

Klute, G.K. et al., "Artificial Muscles: Actuators for Lower Limb Prostheses," Abstract in: Proceedings of the $2^{nd}$ Annual Meeting of the VA Rehabilitation Research and Development Service, Washington, D.C., Feb. 20-22, 2000, p. 107.

Klute, G.K. et al., "Artificial Muscles: Actuators for Biorobotic Systems," *The International Journal of Robotics Research*, vol. 21, pp. 295-309 (2002).

Klute, G.K. et al., "Artificial Muscles: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.

Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.

Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.

Klute, G.K. et al., "Mechanical properties of prosthetic limbs: Adapting to the patient," *Journal of Rehabilitation Research and Development*, vol. 38, No. 3, pp. 299-307 (May/Jun. 2001).

(56) References Cited

OTHER PUBLICATIONS

Klute, G.K. et al., "Muscle-like Pneumatic Actuators for Below-knee Prostheses," "Actuator 2000: 7th International Conference on New Actuators," Bremen, Germany on Jun. 19-21, 2000, pp. 289-292.

Klute, G.K. et al., "Powering Lower Limb Prosthetics with Muscle-like Actuators," Abstract in: Proceedings of the 1st Annual Meeting of the VA Rehabilitation Research and Development Service, "Enabling Veterans: Meeting the Challenge of Rehabilitation in the Next Millenium," Washington, D.C., Oct. 1-3, 1998, p. 52.

Klute, G.K. et al., "Variable Stiffness Prosthesis for Transtibial Amputees," 2 pages.

Koganezawa, K. et al., *Biomedical Engineering 1987*, 2.3: Control Aspects of Artificial Leg, pp. 71-85.

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.

Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).

Kuo, A.D., "A Simple Model of Bipedal Walking Predicts the Preferred Speed-Step Length Relationship," *Transactions of the ASME*, vol. 123, pp. 264-269 (Jun. 2001).

Kuo, A.D., "Energetics of Actively Powered Locomotion Using the Simplest Walking Model," *Journal of Biomechanical Engineering*, vol. 124, pp. 113-120 (Feb. 2002).

Lafortune, M.A., "Three-Dimensional Acceleration of the Tibia During Walking and Running," *J. Biomechanics*, vol. 24, No. 10, pp. 877-886 (1991).

LeBlanc, M.K. et al., "Generation and Transfer of Angular Momentum in the Javelin Throw," American Society of Biomechanics, Presented at the 20th Annual Meeting of the American Society of Biomechanics, Atlanta, Georgia, Oct. 17-19, 1996, 4 pages.

Light, L.H. et al., "Skeletal Transients on Heel Strike in Normal Walking with Different Footwear," J. Biomechanics, vol. 13, pp. 477-480 (1980).

Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.

Lloyd, R. et al., "Kinetic changes associated with load carriage using two rucksack designs," *Ergonomics*, vol. 43, No. 9, pp. 1331-1341 (2000).

Luinge, H.J., *Inertial Sensing of Human Movement*, Twente University Press, Enschede, the Netherlands, 80 pages (Feb. 15, 1973).

Lundberg, A., "Reflex control of stepping," The Norwegian Academy of Science and Letters, The Nansen Memorial Lecture, Oct. 10, 1968, 40 pages.

Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.

Maganaris, C.N., "Force-length characteristics of in vivo human skeletal muscle," *Acta Physiol Scand*, 172: 279-285 (2001).

Maganaris, C.N., "Force-Length Characteristics of the in Vivo Human Gastroenemius Muscle," *Clinical Anatomy*, 16: 215-223 (2003).

Martens, W.L. J., "Exploring the Information Content and Some Applications of Body Mounted Piezo-Resistive Accelerometers," 3 pages.

Maufroy, C. et al., "Towards a general neural controller for quadrupedal locomotion," Neural Networks, 21: 667-681 (2008).

Mayagoitia, R.E. et al., "Accelerometer and rate gyroscope measurement of kinematics: an inexpensive alternative to optical motion analysis systems," *Journal of Biomechanics*, 35: 537-542 (2002).

McFadyen, B.J. et al., "An Integrated Biomechanical Analysis of Normal Stair Ascent and Descent," J. Biomechanics, vol. 21, No. 9, pp. 733-744 (1988).

McGeer, T., "Passive Dynamic Walking," The International Journal of Robotics Research, 9, pp. 62-88 (1990).

McGreer, T., Chapter 4: "Principles of Walking and Running," *Advances in Comparative and Environmental Physiology*, vol. 11, pp. 113-139 (1992).

McIntosh, A.S. et al., "Gait dynamics on an inclined walkway," Journal of Biomechanics, vol. 39, Issue 13, pp. 2491-2502 (2006).

McMahon, T.A. et al., "Groucho Running," pp. 2326-2337 (1987).

McMahon, T.A. et al., "The Mechanics of Running: How Does Stiffness Couple with Speed?" J. Biomechanics, vol. 23, Suppl. 1, pp. 65-78 (1990).

Minassian, K. et al., "Human lumbar cord circuitries can be activated by extrinsic tonic input to generate locomotor-like activity," Human Movement Science, 26: 275-295 (2007).

Mochon, S. et al., "Ballistic Walking," *J. Biomechanics*, vol. 13, pp. 49-57 (1980).

Molen, N.H., "Energy/Speed Relation of Below-Knee Amputees Walking on a Motor-Driven Treadmill," Physiol, 31: 173-185 (1973).

Morris, J.R.W., "Accelerometry—A Technique for the Measurement of Human Body Movements," J. Biomechanics, vol. 6, pp. 729-736 (1973).

Muraoka, T. et al., "Muscle fiber and tendon length changes in the human vastus lateralis during show pedaling," J. Appl. Physiol., 91: 2035-2040 (2001).

Nakagawa, A., "Intelligent Knee Mechanism and the Possibility to Apply the Principle to the Other Joints," paper presented at the Proceedings of the 20th Annual International Conference of the IEEE Engineering in Medicine and Biology Society, 20(5): 2282-2287 (1998).

Neal, R. M. et al., "A View of the EM Algorithm That Justifies Incremental, Sparse, and Other Variants," pp. 1-14.

Ng, S.K. et al., "Fuzzy Model Identification for Classification of Gait Events in Paraplegics," IEEE Transactions on Fuzzy Systems, 5(4) (1997).

Nielsen, D.H. et al., "Comparison of Energy Cost and Gait Efficiency during Ambulation in Below-Knee Ampuees Using Different Prosthetic Feet," *JPO*, 1:24-31, http://www.oandp.org/jpo/library/1989_01_024.asd, Retrieved on: Feb. 7, 2012.

Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).

Ogihara, N., and Yamazaki, N., "Generation of Human Bipedal Locomotion by a Bio-Mimetic Neuro-Musculo-Skeletal Model," *Biol. Cybern.*, 84: 1-11 (2001).

Palmer, M.L., "Sagittal Plane Characterization of Normal Human Ankle Function Across a Range of Walking Gait Speeds," Unpublished master's thesis, Massachusetts Institute of Technology, Massachusetts (2002).

Paluska, D., and Herr, H., "Series Elasticity and Actuator Power Output," paper presented at the Proceedings of the 2006 IEEE International Conference on Robotics and Automation (2006).

Paluska, D., and Herr H., "The Effect of Series Elasticity on Actuator Power and Work Output: Implications for Robotic and Prosthetic Joint Design," Robotics and Autonomous Systems, 54:667-673 (2006).

Pang, M.Y.C. and Yang, J.F., "The Initiation of the Swing Phase in Human Infact Stepping: Importance of Hip Position and Leg Loading," *Journal of Physiology*, 528(2):389-404 (2000).

Dubowsky, S., "Transactions of the ASME," *Journal of Mechanisms, Transmissions, and Automation in Design*, 106(1): 102-107 (1984).

Paul, C., et al., "Development of a Human Neuro-Musculo-Skeletal Model for Investigation of Spinal Cord Injury," *Biol. Cybern.*, 93:153-170 (2005).

Pearson, K., et al., "Assessing Sensory Function in Locomotor Systems Using neurp-mechanical Simulations," *Trends in Neurosciences*, 29(11): 626-631 (2006).

Pearson, K.G., "Generating the Walking Gait: Role of Sensory Feedback," Progress in Brain Research, 143:123-129 (2004).

Perry, J., et al., "Efficiency of Dynamic Elastic Response Prosthetic Feet," *Journal of Rehabilitation Research*, 30(1):137-143 (1993).

(56) References Cited

OTHER PUBLICATIONS

Davids, J.R., "Book Reviews" Journal of Pediatric Orthopedics, pp. 815, No date given.
Petrofsky, J.S.., et al., "Feedback Control System for Walking in Man," *Comput. Biol. Med.* 14(2):135-149 (1984).
Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).
Popovic, M., et al., "Angular Momentum Primitives for Human Walking: Biomechanics and Control," paper presented at the Proceedings IEEE/RSJ International Conference on Intelligent Robots and Systems, 1685-1691 (2004).
Popovic, M., et al., "Angular Momentum Regulation During Human Walking: Biomechanics and Control," paper presented at the Proceedings IEEE International Conference on Robotics and Automation, 2405-2411 (2004).
Popovic, M., et al., "Conservation of Angular Momentum During Human Locomotion," *MIT Artificial Intelligence Laboratory*, pp. 231-232 (2002).
Popovic, D., et al., "Control Aspects of Active Above-Knee Prosthesis," *Int. J. Man-Machine Studies*, 35:751-767 (1991).
Popovic, D. and Sinkjaer, T., "Control of Movement for the Physically Disabled: Control for Rehabilitation Technology," (Springer Publisher) pp. 270-302, No date given.
Popovic, M.R., et al., "Gait Identification and Recognition Sensor," paper presented at the Proceedings of $6^{th}$ Vienna International Workshop on Functional Electrostiumlation (Sep. 1998).
Popovic, M.B. and Herr, H., "Global Motion Control and Support Base Planning," pp. 1-8.
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," pp. 1-16.
Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Pratt, G.A. and Williamson, M.M., "Series Elastic Actuators." Paper presented at the meeting of the IEEE, pp. 399-406 (1995).
Prochazka, A. and Yakovenko, S., "The Neuromechanical Tuning Hypothesis," *Progress in Brain Research*, 165: 257-267 (2007).
Prochazka, A., et al., "Sensory Control of Locomotion: Reflexes Versus Higher-Level Control," *Sensorimotor Control of Movement and Posture*, pp. 357-367 (2002).
Prochazka, A., et al., "Positive Force Feedback Control of Muscles," *The American Physiological Society*, pp. 3226-3236 (1997).
Raibert, M.H., "Legged Robots that Balance," MIT Press, Cambridge, MA, p. 89 (1985).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).
Robinson, D.W., "Design and Analysis of Series Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man, and Cybernetics—Part A: Systems and Humans*, 31(3): 210-222 (2001).
Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2): 617-639 (2006).
Rybak, I.A., et al., "Modelling Spinal Circuitry Involved in Locomotor Pattern Generation: Insights from the Effects of Afferent Stimulation," *J. Physiol.*, 577(2): 641-658 (2006).
Sanderson, D.J. and Martin. P.E., "Lower Extremity Kinematic and Kinetic Adaptations in Unilateral Below-Knee Amputees During Walking," *Gait & Posture*, 6(2): 126-136 (1997).
Sanger, T.D., "Human Arm Movements Described by a Low-Dimensional Superposition of Principal Components," *The J. of Neuroscience*, 20(3): 1066-1072 (2000).
Saranli, U., et al., "RHex: A Simple and Highly Mobile Hexapod Robot," *The International Journal of Robotics Research*, pp. 616-631 (2001).
Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).
Schaal, S. and Atkeson, C.G., "Constructive Incremental Learning from Only Local Information," *Neural Computation*, 10(8): 2047-2084 (1998).
Schaal, S., "Is Imitation Learning the Route to Humanoid Robots?", *Trends in Cognitive Sciences*, 3: 233-242 (1999).
Scott, S.H. and Winter, D.A., "Biomechanical Model of the Human Foot: Kinematics and Kinetics During the Stance Phase of Walking," *J. Biomechanics*, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16.
Seyfarth, A., et al., "A Movement Criterion for Running," *J. of Biomechanics*, 35: 649-655 (2002).
Seyfarth, A., et al., "Stable Operation of an Elastic Three-Segment Leg," *Biol. Cybern.*, 84: 365-382 (2001).
Seyfarth, A., et al., "Swing-Leg Retraction: A Simple Control Model for Stable Running," *The J. of Experimental Biology*, 206: 2547-2555 (2003).
Giszter et al., "Convergent Force Fields Organized in the Frog's Spinal Cord," The Journal of Neuroscience, Feb. 1993, pp. 467-491.
Sinkjaer, T., et al., "Major role for sensory feedback in soleus EMG activity in the stance phase of walking in man," *Journal of Physiology*, 523.3: 817-827 (2000).
Skinner, H.B., and Effeney, D.J., "Gait Analysis in Amputees," *American Journal of Physical Medicine*, 64(2): 82-89 (1985).
Smidt, G.L., et al., "An Automated Accelerometry System for Gait Analysis," *J. Biomechanics*, 10: 367-375 (1977).
Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5.
Stepien, J., et al., "Activity Levels Among Lower-Limb Amputees: Self-Report Versus Step Activity Monitor," *Arch. Phys. Med. Rehabil.*, 88: 896-900 (2007).
Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).

(56) References Cited

OTHER PUBLICATIONS

Sup, F., et al., "Design and Control of a Powered Transfemoral Prosthesis," *The International Journal of Robotics Research*, 27(2): 263-273 (2008).
Taga, G., "A model of the neuro-musculo-skeletal system for human locomotion," *Biol. Cybern.*, 73: 97-111 (1995).
Takayuki, F., et al., "Biped Locomotion using Multiple Link Virtual Inverted Pendulum Model," *T.IEE Japan*, 120-C (2): 208-214 (2000).
Thoroughman, K., and Shadmehr, R., "Learning of action through adaptive combination of motor primitives," *Nature*, 407: 742-747(2000).
Tomović, R., and McHee, R.B., "A Finite State Approach to the Synthesis of Bioengineering Control Systems," *IEEE Transactions on Human Factors in Electronics*, 7(2): 65-69 (1966).
Tong, K., and Granat, M., "A practical gait analysis system using gyroscopes," *Medical Engineering & Physics*, 21: 87-94 (1999).
Türku, K., "Electromyography: Some Methodological Problems and Issues," *Phys. Ther.*, 73: 698-710 (1993).
Van den Bogert, A. J., et al., "A Method for Inverse Dynamic Analysis Using Accelerometry," *J. Biochemechanics*, 29(7): 949-954 (1996).
Van den Bogert, A. J., "Exotendons for Assistance of Human Locomotion," *Biomedical Engineering OnLine*, BioMed Central, 2(17):1-8 (2003).
Veltink, P.H., et al., "The Feasibility of Posture and Movement Detection by Accelerometry," paper presented at the IEEE meeting (1993).
Vukobratovic, M., Juricic, D., "Contribution to the Synthesis of Biped Gait," paper presented at the IEEE Transactions on Bio-Medical Engineering, BME-16(1) (Jan. 1969).
Vukobratovic, M., and Stepanenko, J., :Mathematical Models of General Anthropomorphic Systems, Mathematical Biosciences, 17: 191-242 (1973).
Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).
Waters, R.L., et al., "Energy Cost of Walking of Amputees: The Influence of Level of Amputation," *The Journal of Bone and Joint Surgery*, 58A(1): 42-46 (1976).
Wilkenfeld, A., and Herr, H., "An Auto-Adaptive External Knee Prosthesis," MIT Lab., No date given.
Wilkenfeld, A., "Biologically Inspired Autoadaptive Control of a Knee Prosthesis," unpublished doctoral dissertation, Massachusetts Institute of Technology, Cambridge, MA (2000).
Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).
Willemsen, A.Th.M., et al.. "Real-Time Gait Assessment Utilizing a New Way of Accelerometry," *J. Biomechanics*, 23(8):859-863 (1990).
Williams, B.C., et al., "Mode Estimation of Model-Based Programs: Monitoring Systems with Complex Behavior," paper submitted to Massachusetts Institute of Technology, Cambridge, MA, No date given.
Williamson, M.M., "Series Elastic Actuators," A.I. Technical Report submitted to Massachusetts Institute of Technology, Cambridge, Massachusetts (Jan. 1995).
FF, D.A., and Sienko, S.E., "Biomechanics of Below-Knee Amputee Gait," *J. Biomechanics*, 21(5):361-367 (1988).
Winter, D.A., "Energy Generation and Absorption at the Ankle and Knee during Fast, Natural, and Slow Cadences," *Clinical Orthopedics and Related Research*, 175: 147-154 (1983).
Winter, D.A., and Robertson, D.G.E., "Joint Torque and Energy Patterns in Normal Gait," Biol. Cybernetics, 29:137-142 (1978).
Wisse, M., "Essentials of Dynamic Walking: Analysis and Design of Two-legged Robots," No date given.
Woodward, M.I. and Cunningham, J.L., "Skeletal Accelerations Measured During Different Exercises," *Proc. Instn. Mech. Engrs.*, 207: 79-85 (1993).
Wu, G. and Ladin, Z., "The Study of Kinematic Transients in Locomotion Using the Integrated Kinematic Sensor," *IEEE Transactions on Rehabilitation Engineering*, 4(3): 193-200 (1996).
Yakovenko, S., et al., "Contribution of Stretch Reflexes to Locomotor Control: A Modeling Study," *Biol. Cybern.*, 90: 146-155 (2004).
Yun, X., "Dynamic State Feedback Control of Constrained Robot Manipulators." Paper presented at the Proceedings of the 27$^{th}$ Conference on Decision and Control, Austin, TX (Dec. 1988).
Zlatnik, D., et al., "Finite-State Control of a Trans-Femoral (TF) Prosthesis," *IEEE Transactions on Control Systems Technology*, 10(3): 408-420 (2002).
Vannah, William M., and Childress, Dudley S., "Indentor tests and finite element modeling of bulk muscular tissue in vivo," *J. Rehab. Res. Dev.*, 33(3):239-252 (1996).

\* cited by examiner ns and the government has certain rights in the invention.

PHYSIOLOGICAL MEASUREMENT DEVICE OR WEARABLE DEVICE INTERFACE SIMULATOR AND METHOD OF USE

RELATED APPLICATION(S)

This application claims the benefit of U.S. Provisional Application No. 61/576,275, filed on Dec. 15, 2011.

The entire teachings of the above application are incorporated herein by reference.

GOVERNMENT SUPPORT

This invention was made with government support under VA118-12-C-0040 from United States Department of Veterans Affairs. The government has certain rights in the invention.

BACKGROUND OF THE INVENTION

Body-attachable devices employed to support a subject at, for example, a limb or the terminal end of a residual limb, often cause significant problems consequent to uneven distribution of force at surface areas of the subject in contact with the supporting orthosis or prosthesis. Although orthoses and prostheses typically are fitted by forming a material to the contours of the area of contact with the subject, soft tissue tends to move under use conditions consequent to linear and non-linear changes and differences in load, impedance and stiffness across the interface between the orthosis or prosthesis and the subject. Such changes of the soft tissue underlying the interface redistributes force across the area of the orthosis or prosthesis contacting the subject and can, as a consequence, deleteriously affect the subject not only in the area of contact with the prosthesis but, secondarily, as a result of efforts by the subject to minimize discomfort caused by that uneven distribution of force during activity. Previous attempts to minimize uneven distribution of force across the contact area between a subject and a prosthesis have included, for example, bladders that are distributed across the surface area of the prosthesis contacting the subject. However, such attempts generally do not account for differences in load, impedance or stiffness across the interface between an orthosis or prosthesis and a subject and, therefore, cannot be manipulated to correct the types of forces distributed across the interface.

Therefore, a need exists to overcome or minimize the above-referenced difficulties.

SUMMARY OF THE INVENTION

The invention generally is directed to a physiological measurement device or wearable device simulator, and to a method for measuring a physiological feature of a subject, or simulating an interface of a wearable device.

In one embodiment, the invention is a physiological measurement device or wearable device simulator that includes a frame and a plurality of surfaces distributed within the frame. For each surface, a surface actuator links the surface to the frame, whereby i) forces applied by the surfaces to the subject, and ii) the position of the surfaces relative to each other and relative to the subject, can be modulated independently of each other, thereby measuring the physiological feature of the subject or simulating a wearable device interface.

In another embodiment, the invention is a method for measuring a physiological feature of a subject or simulating an interface of a wearable device, including the steps of placing a plurality of surfaces against a subject, at least a portion of the surfaces being linked to a frame by an actuator, and modulating independently of each other at least one of: i) the forces applied by the surfaces to the subject; and ii) the position of the surfaces relative to each other and relative to the subject, thereby measuring the physiological feature of the subject or simulating an interface of a wearable device.

This invention has many advantages. For example, by fixing the position of at least a portion of the surfaces, independently of the forces applied by or to the surface, a physiological feature of the subject at the surface can be modeled or measured, and the interface between a wearable device, such as an orthosis or a prosthesis, and the subject, can be simulated with increased accuracy.

DETAILED DESCRIPTION OF THE INVENTION

A description of example embodiments of the invention follows.

The invention generally is directed to a physiological measurement device or wearable device interface simulator. The invention is also directed generally to a method for measuring a physiological feature of a subject or simulating an interface of a wearable device.

Figure 1:
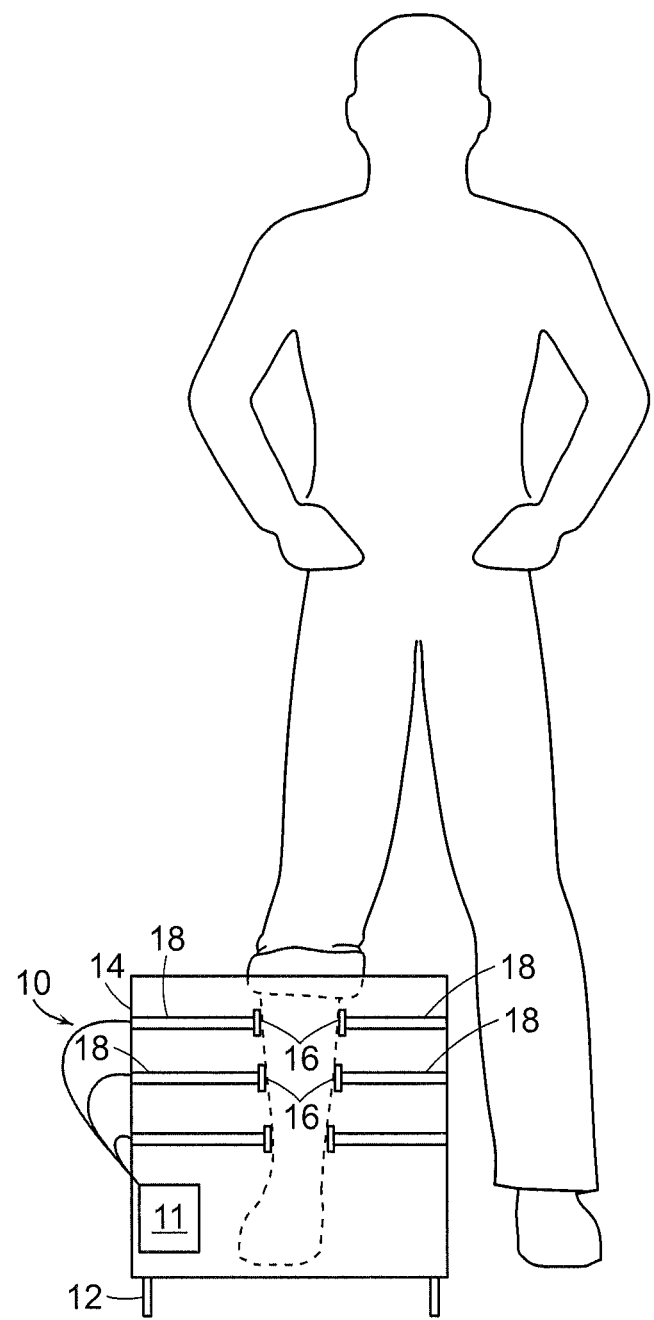
FIG. 1 is a representation of one embodiment of the invention while it is fixed in space relative to a subject.

In one embodiment of the invention, shown in FIG. 1, physiological measurement device or wearable device interface simulator 10 includes support component 12 that fixes frame 14 relative to any or all of: i) a fixed point in space; ii) a skeletal feature of a subject proximate to a surface of the subject to be simulated or measured, and iii) the surface of the subject to be simulated or measured. Typically, support component will include rods and straps, as necessary, to minimize relative movement between frame and the physiological feature of the subject to be simulated or measured. A plurality of surfaces 16 are distributed within frame 14. Surface actuator 18 links each surface to frame 14. Surfaces 16 can be separated from each other, contiguous with each other, or overlap with each other. Controller 11 is linked to surface actuators 18 and can be employed to coordinate modulation of surface actuators, either independently or in response to sensors, such as sensors at surfaces 16, or as more completely described below.

Figure 2:
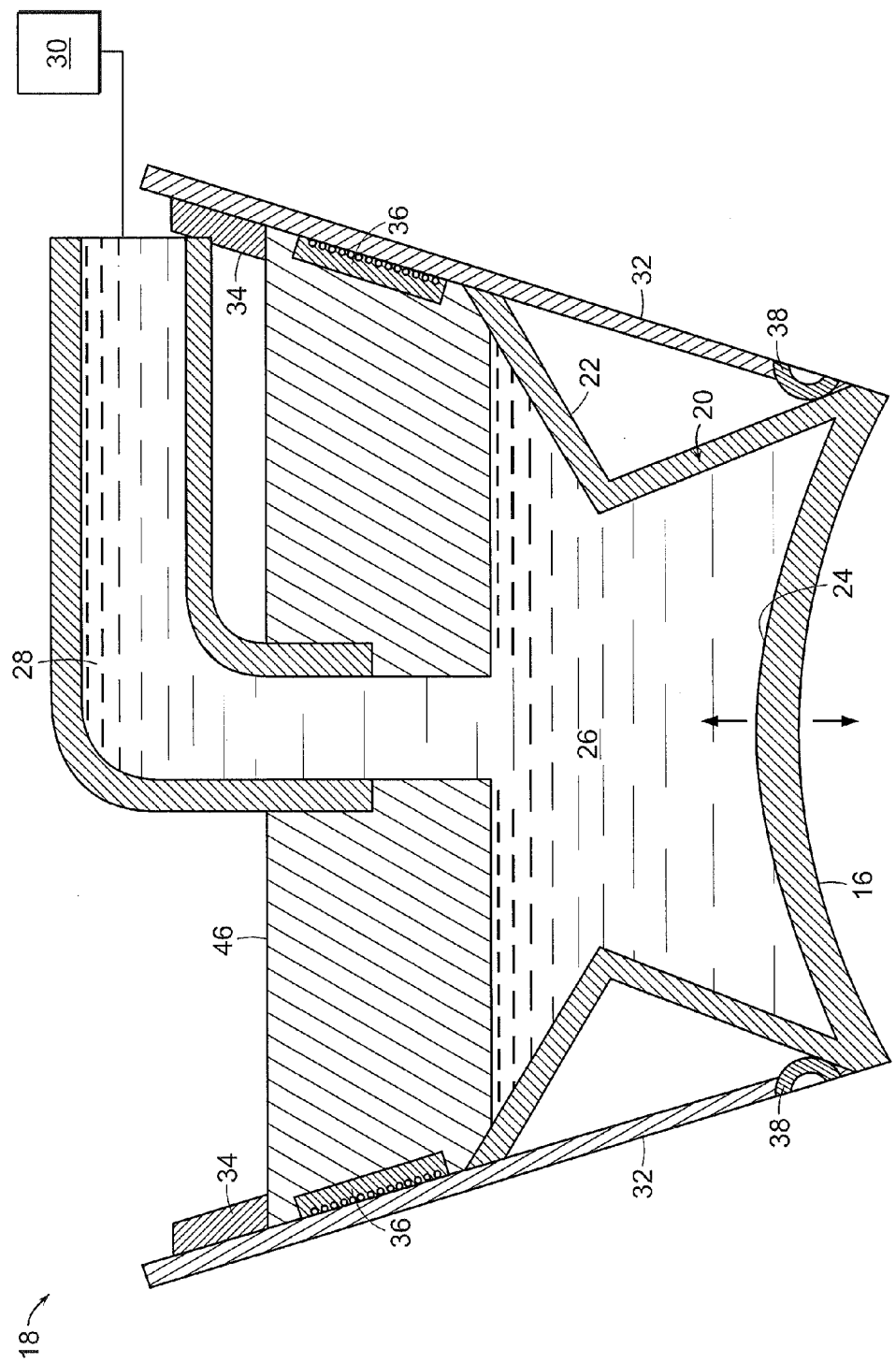
FIG. 2 is a cross-sectional view of one embodiment of an actuator suitable for use in the invention.

One embodiment of a suitable surface actuator is shown in FIG. 2. As shown therein, bladder 20 of surface actuator 18 includes bellows 22, diaphragm 24 and frame 46 that define chamber 26. Surface 16 is defined by diaphragm 24. Conduit 28 extends from chamber 26 to fluid source 30. Chamber 26 is filled with a fluid, such as an incompressible liquid, a gas, a gel, or a combination of such fluids. Bellows 22 is supported at a periphery of diaphragm 24 by at least one rod 32 linking the periphery of diaphragm 24 to potentiometer 34 mounted remotely from diaphragm 24. Linear bearing 36 interposed between rod 32 and bellows 22 provides support for rod 32 without interfering with readings by potentiometer 34. Gasket 38 is interposed between diaphragm 24 and rod 32 to ensure flexibility of surface 16 at diaphragm 24 in conforming with a physiological feature of a subject to be simulated or measured.

In operation, the volume of chamber 26 of bladder 20 can be changed by force applied by a subject contacting surface 16 of diaphragm 24 or can be modulated in response to feedback from surface actuator 18, such as in response to readings of potentiometer 34. "Modulation," as that term is defined herein, means control or monitoring of a feature, such as pressure, force or position. The volume of chamber 26 can be modulated by changing the volume of liquid within chamber 26 through conduit 28. The conduits extending from the bladders of surface actuators 18 are connected through a closed loop control system, whereby the position of surface 16 can be precisely monitored, and, independently, the position of surface 16 can be modulated by modulating the volume of chamber 26 to control the position of surface 16.

Optionally, or alternatively, sensors other than potentiometer 34 can be employed in surface actuator 18. Examples of such sensors include series elastic actuators, ultrasound sensors capacitive sensors, temperature sensors, infrared optical sensors, linear actuators, visible spectrum optical sensors, fluid pressure sensors, reed switch sensors, inductive sensors and electromyographic sensors, and can be located relative to surface 16 as appropriate.

Figure 3:
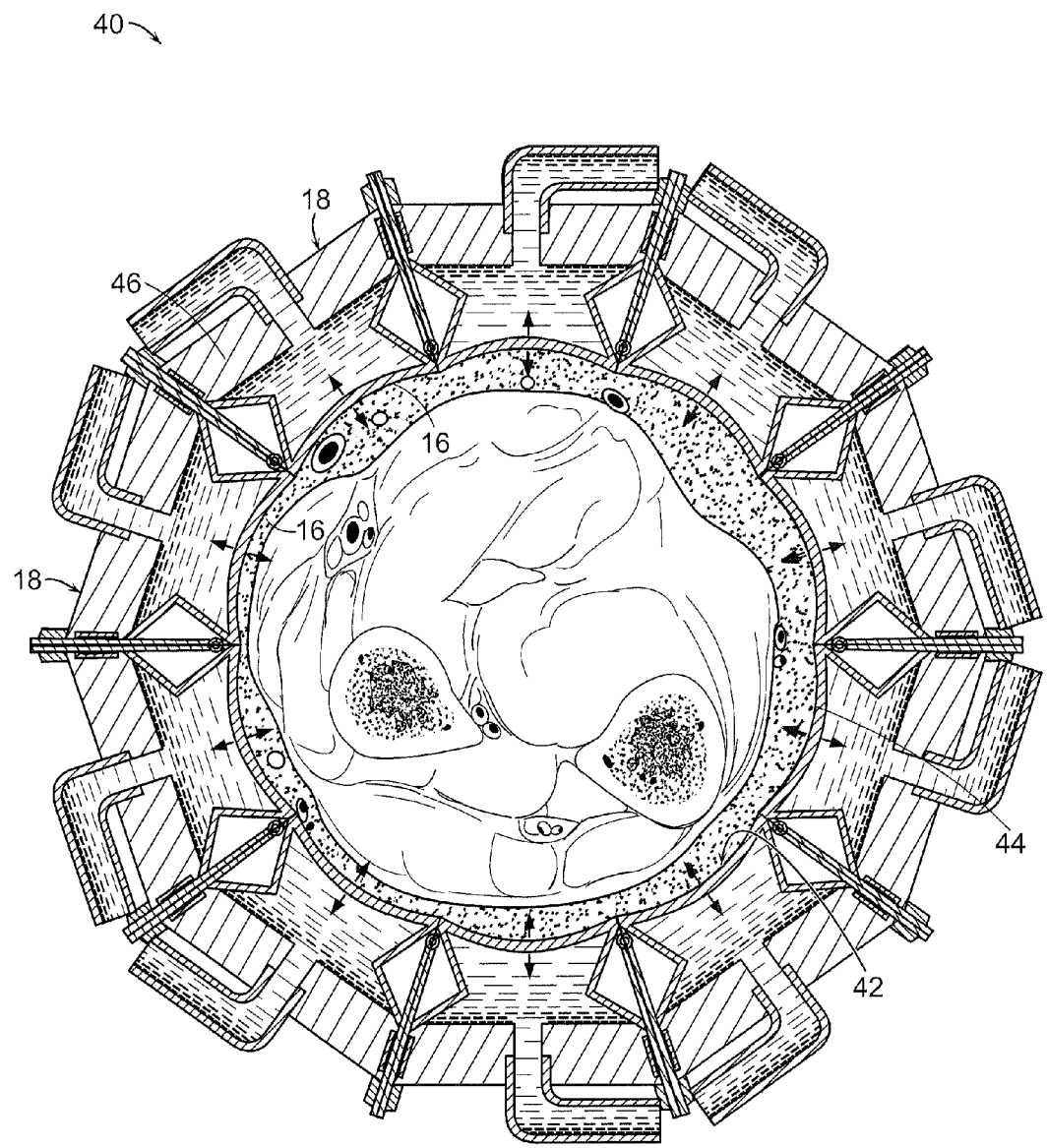
FIG. 3 is a cross-sectional view of one embodiment of the invention, including an array of actuators of the type shown in FIG. 2.

In another embodiment, shown in FIG. 3, array 40 of surface actuators 18 define socket 42 at surfaces 16. Surfaces 16 are contiguous and define socket 42 into which residual limb 44 or other appendage or surface of the subject may be inserted for physiological simulation and measurement of the surface of the subject. Surface actuators 18 are supported by frame 46, which can be integral to individual surface actuators 18 and can support other surface actuators 18 by virtue of surface actuators 18 being linked together, as shown in FIG. 3. Alternatively, the frame can be a superstructure (not shown) to which surface actuators 18 are mounted.

Arrays of surface actuators 18 can take different forms. For example, surface actuators 18 can be distributed in a plane and around a periphery of an appendage of the subject, as shown in FIG. 3. As previously stated, an array of surface actuators 18 can define, at least in part, a socket or shape into which a residual limb, appendage or subject surface is inserted or applied for physiological simulation and measurement. Optionally, more than one layer of surface actuators 18 are mounted to thereby form a three-dimensional array of sensors, wherein each sensor is associated with a surface actuator, as shown in FIG. 1, and whereby the surfaces define a shape such that the surfaces make contact with a subject's body.

Although shown as contiguous surfaces in FIG. 3, surface actuators 18 can be separated from each other and still linked by a single frame to which they are mounted. Frame 46, as stated above, can be mounted by suitable support components to a subject to thereby substantially prevent movement of the support proximate to the surface or physiological feature of the subject to be simulated or measured, or relative to a physiological skeletal feature of the subject. In another embodiment, while surface actuators 18 are fixed to frame 46, the shape of frame 46 can be modulated to change the distribution of surface actuators 18 relative to each other, either as a consequence of manual control by an operator of the physiological simulation and measurement device, or by operation of other actuators between surface actuators 18 or between the frame and surface actuators in response to feedback from physiological features measured or sensed by sensors at surface actuators 18.

Further, modulation of frame 46 and surface actuators 18, either separately or in combination, can be conducted essentially in real-time, either by actions of the operator of the device of the invention, or in response to feedback from sensors at surface actuators 18. Such modulation can be conducted while the subject remains motionless, or in response to changes in the surface of the subject contacting surfaces at surface actuators 18 while the subject is modulating his position, such as by walking or running, or in response to spontaneous muscle contraction proximate to the surfaces contacting surfaces of surface actuators 18. The data collected as a consequence of feedback from sensors at the surface actuators 18 can be compiled to simulate changes in a surface of a subject, either while the subject is motionless, or during normal activity of the subject, to thereby permit fabrication of, for example, a socket or shape of an orthosis or prosthesis for the subject that minimizes trauma at the orthosis or prosthesis, thereby maximizing the comfort of the subject while wearing the orthosis or prosthesis.

Figure 4:
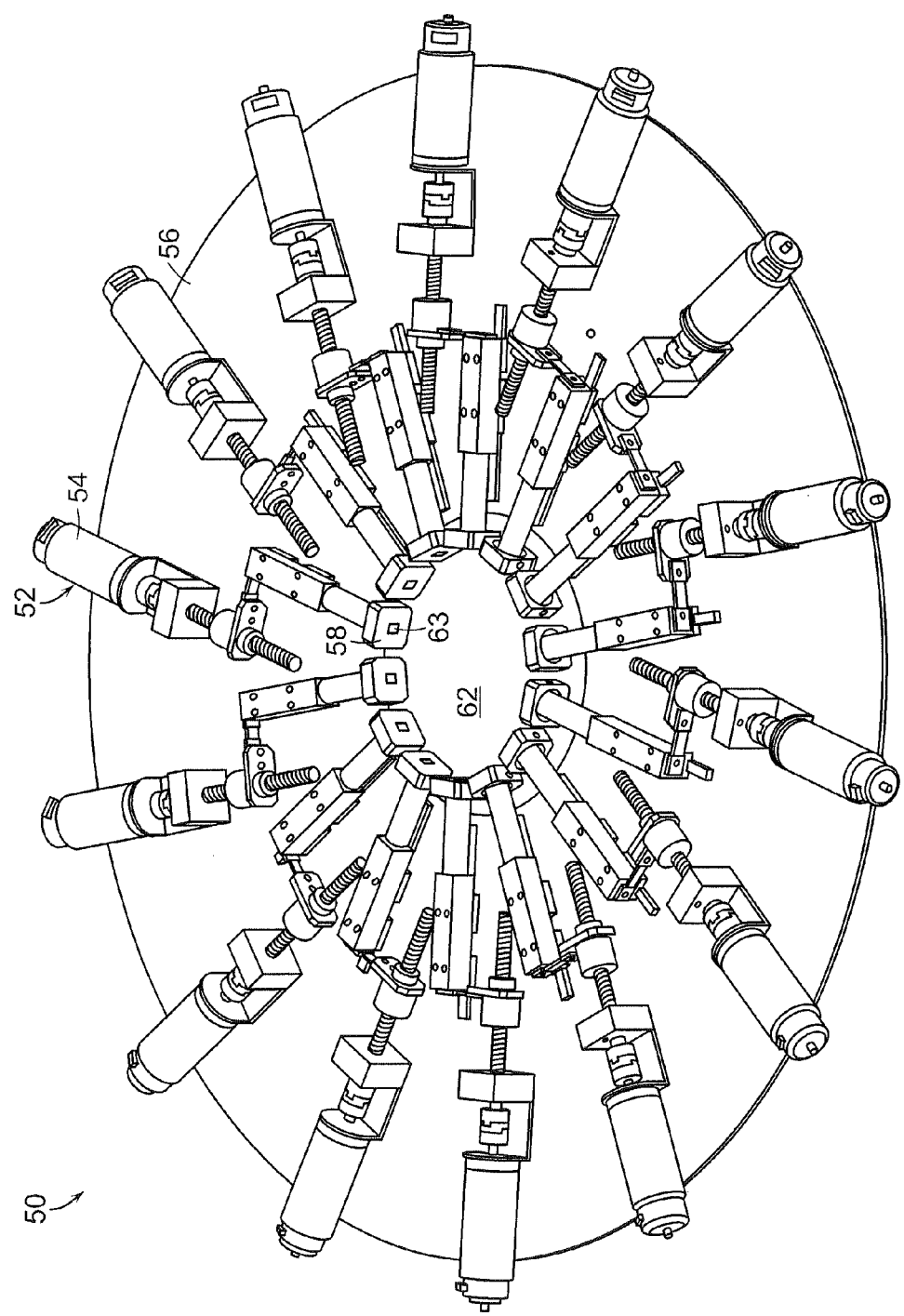
FIG. 4 is a plan view of another embodiment of the invention, including a two-dimensional array of actuators, each of which employs a motor.
Figure 5A:
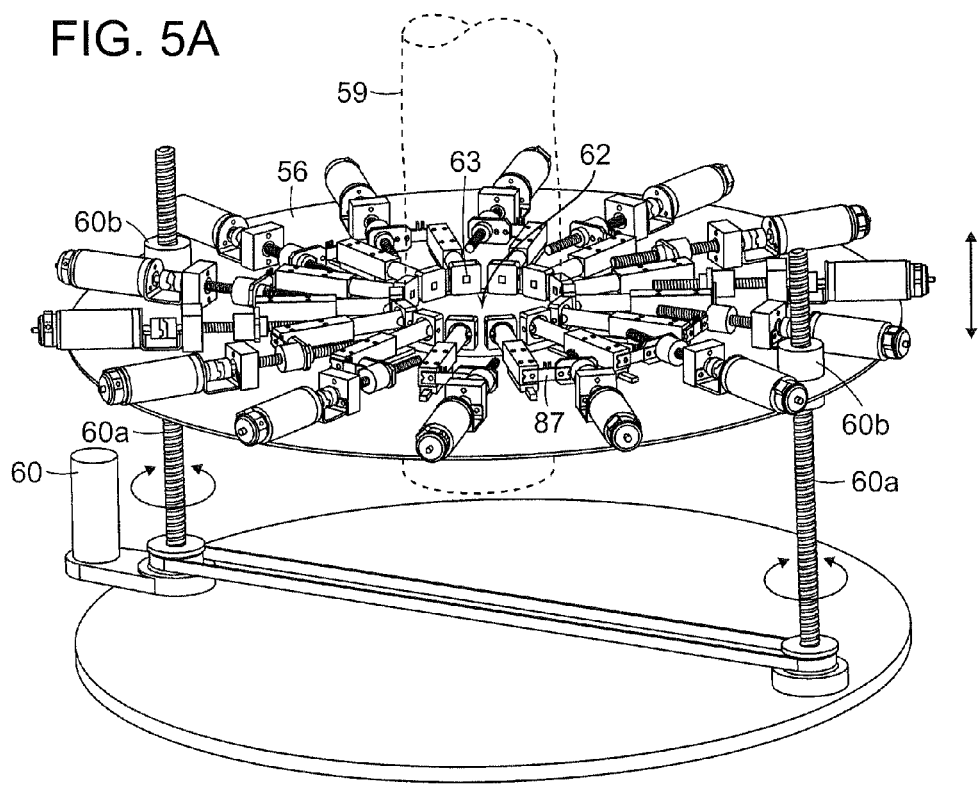
FIGS. 5 and 5B are perspective views of another embodiment of the invention, wherein the array of actuators shown in FIG. 4 can be moved along a subject by use of at least one frame actuator.
Figure 5B:
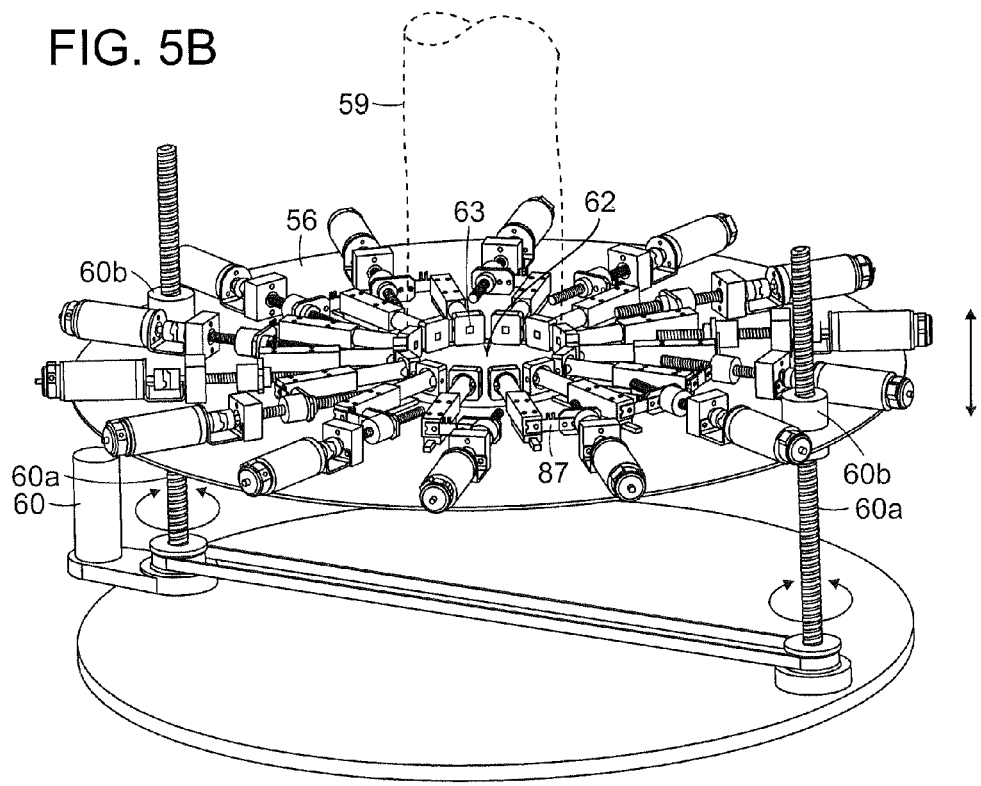
Figure 6:
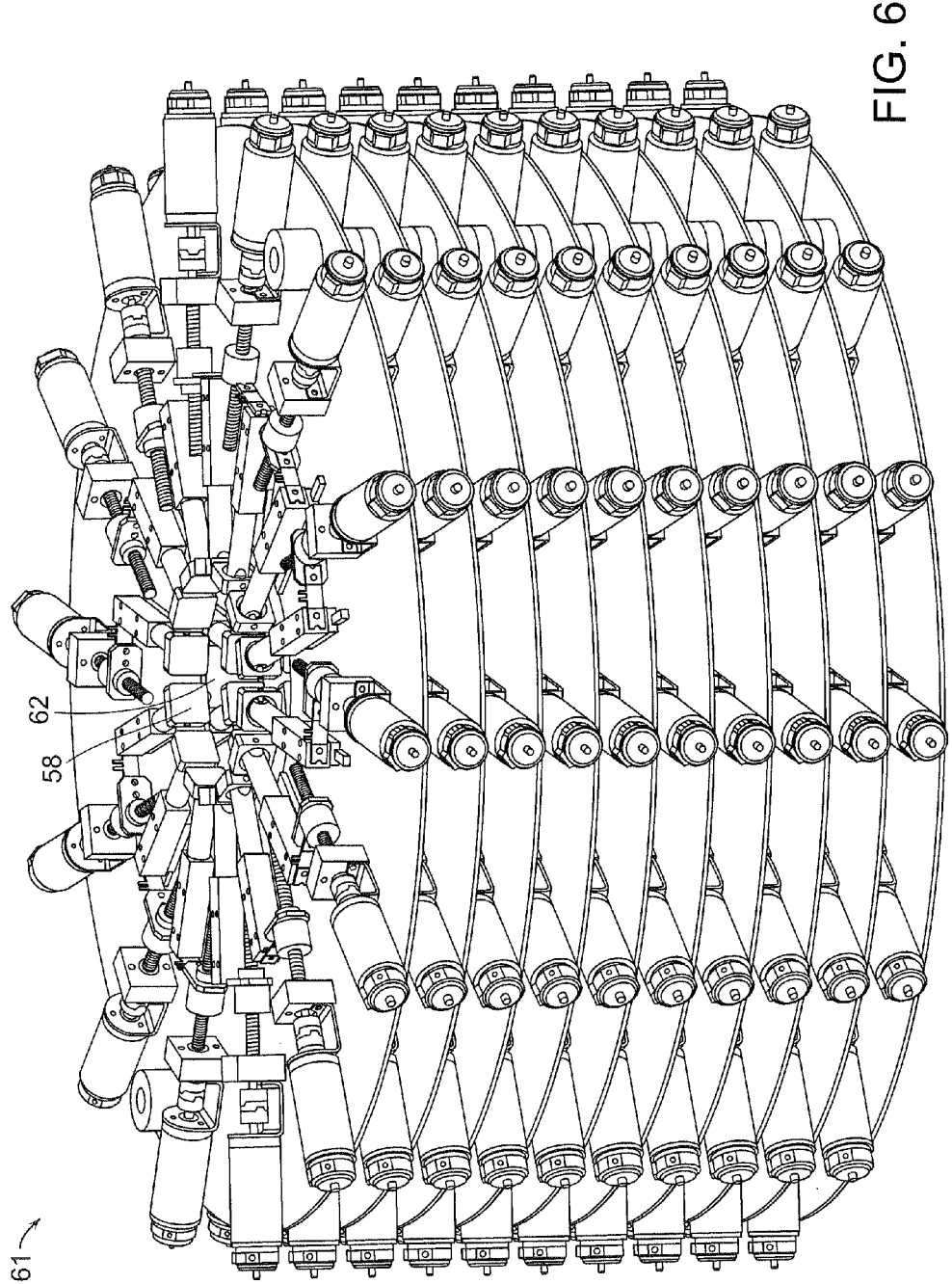
FIG. 6 is a perspective view of another embodiment of the invention employing a three-dimensional array of the actuators shown in FIG. 4.
Figure 7A:
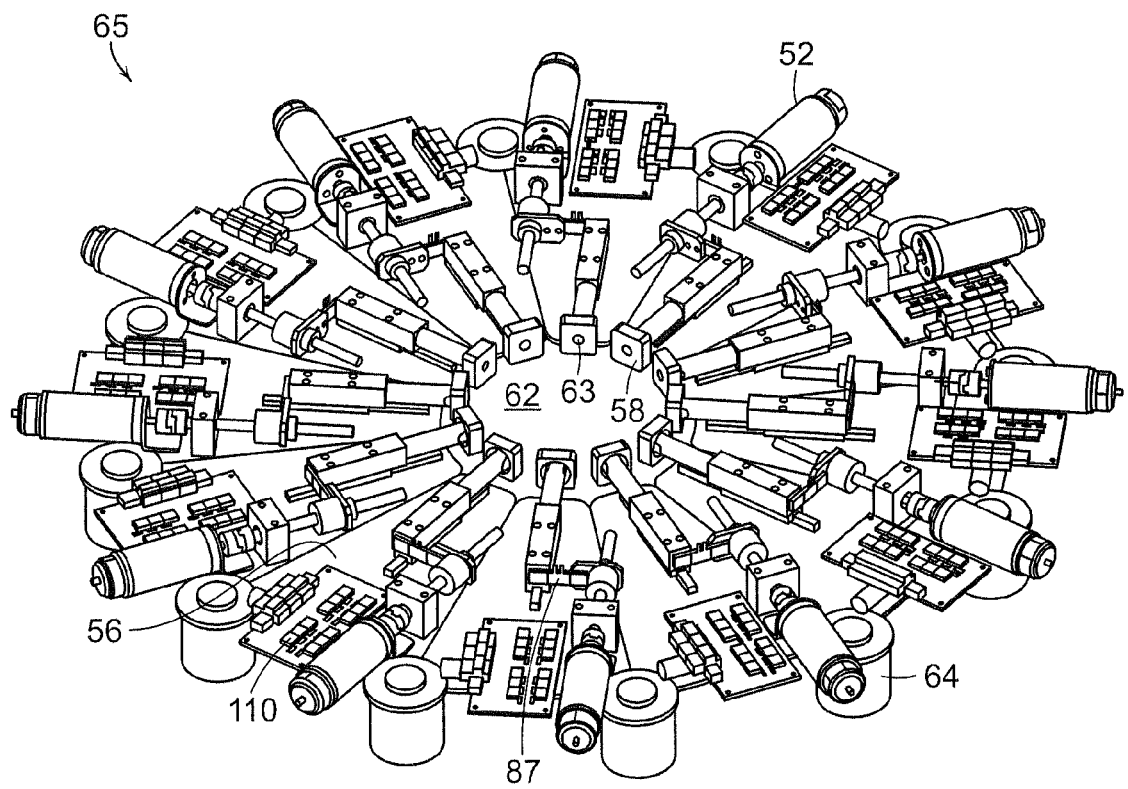
FIGS. 7A-7D are perspective views of an embodiment of the invention employing interstitial actuators.
Figure 7B:
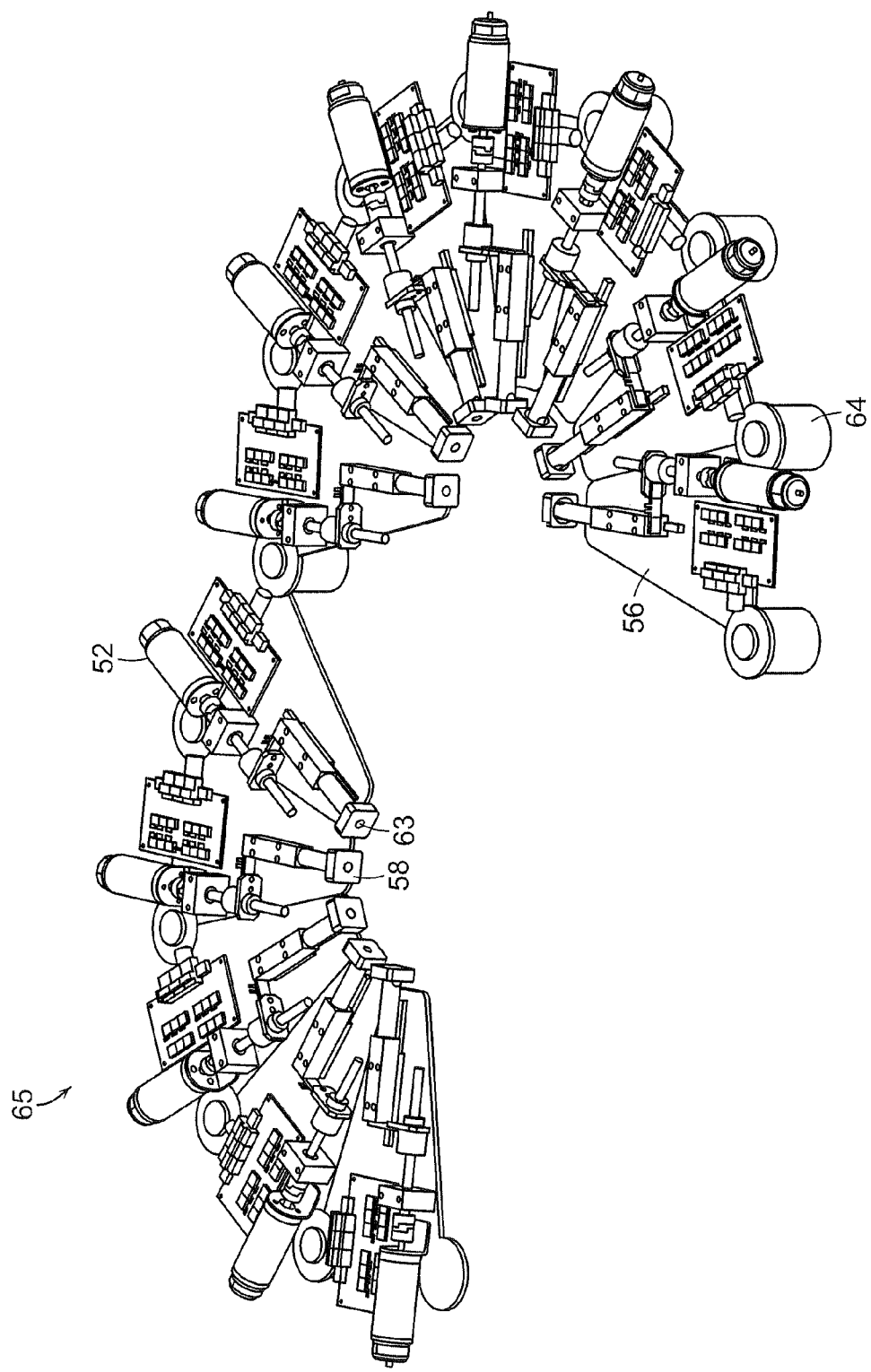
Figure 7C:
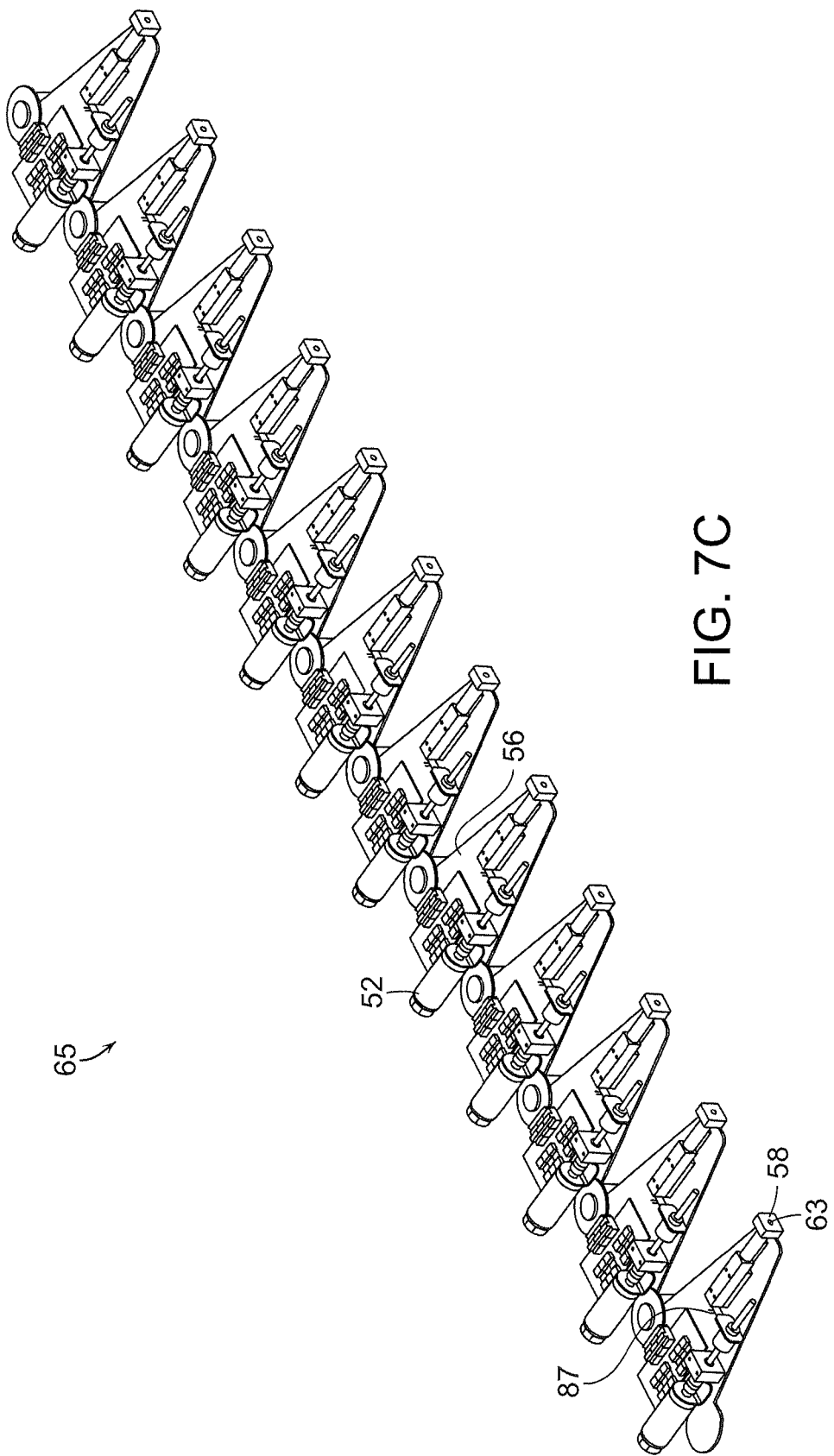
Figure 7D:
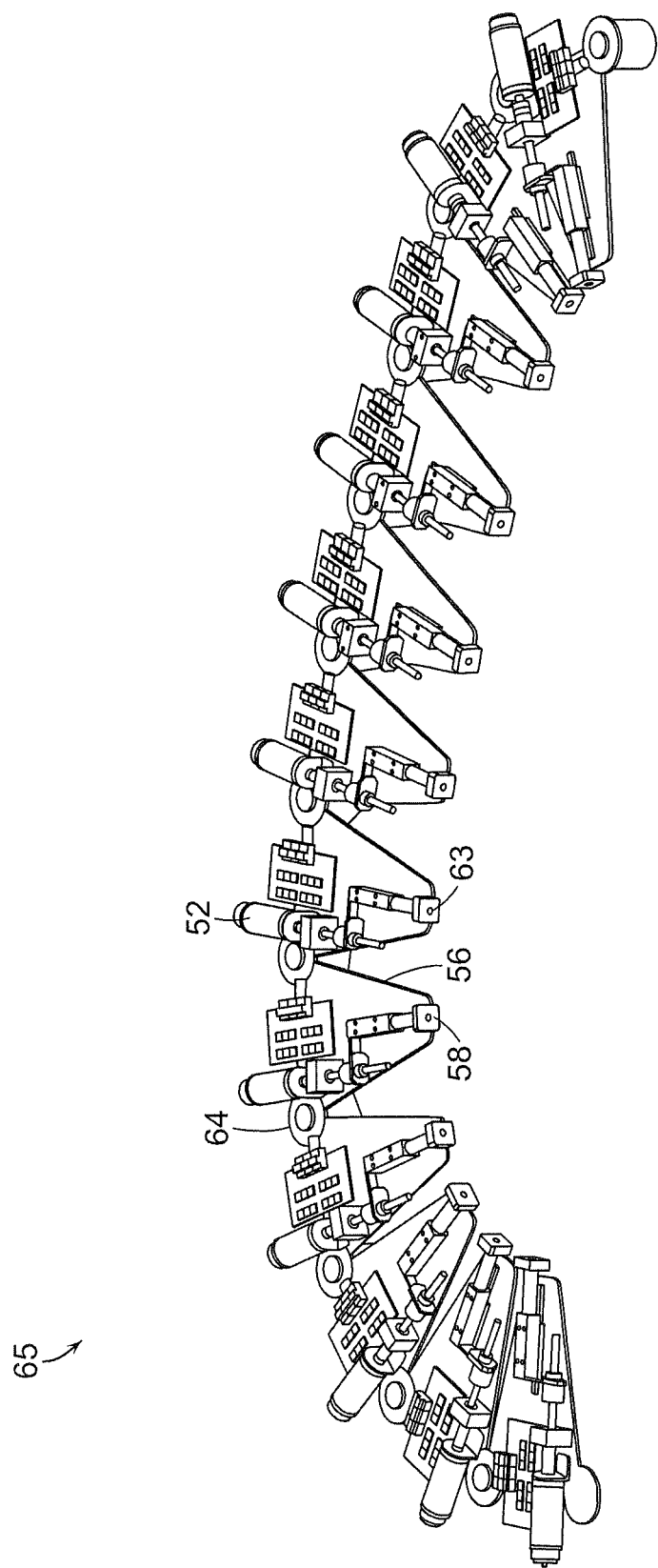

Surface actuators employed in the device of the invention can take many forms. For example, as an alternative to the bladders discussed above with reference to FIGS. 2 and 3, another type of surface actuator can employ a rotary motor to modulate a surface. In one embodiment, shown in FIG. 4, two-dimensional array 50 includes surface actuators 52 based on rotary motors 54. In this embodiment, a two-dimensional image can be constructed by use of surface actuators 52 fixed to frame 56 and that support surfaces 58. Sensors 63 can be located at surfaces 58, or elsewhere, depending on the type of sensor to be employed. Moving the plane of surface actuators 52 and surfaces 58 along an axis substantially normal to the plane of actuators 52 and surfaces 58 can create a three-dimensional image or simulation of an interface between a wearable device and subject 59. Such movement can be conducted by frame actuator 60, as shown in FIGS. 5A and 5B. As can be seen by comparison of FIGS. 5A and 5B, actuation of frame actuator 60 causes rotation of threaded support 60*a* within blocks 60*b* to thereby raise or lower frame 56. Alternatively, a plurality of such two-dimensional arrays can be stacked to form a three-dimensional array 61 of surfaces 58 defining socket 62, as shown in FIG. 6. It is to be noted that a two-dimensional array, as shown in FIGS. 4 and 5, would also define socket 62.

Surface actuators 52 of another embodiment of the invention, array 65, shown in FIGS. 7A-7D, are fixed to frame 56. In one embodiment, surface actuators 52 form a virtual frame by being linked to another, either directly or through interstitial actuators 64 that are configured to move surface actuators 52 relative to each other, as shown in FIGS. 7A through 7D. In this embodiment, frame 56 can be modulated to change the distribution of position of surfaces 58 relative to each other, either as a result of manual control by the operator of the physiological simulation measurement device invention, or as a result of feedback from sensors 64 at surfaces 58, or from another sensor, such as strain gauge 87, at, or supported by, surface actuators 52. Surface actuators 52 can be controlled by circuits 110. Circuits 110 can be collectively controlled by linking them together, such as through a controller, as shown in FIG. 1.

Figure 8A:
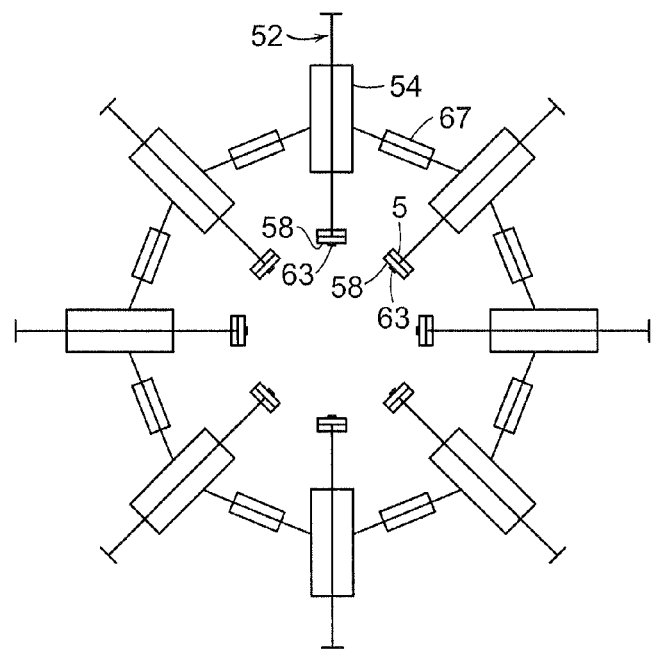
FIGS. 8A and 8B are schematic representations of another embodiment of the invention employing interstitial actuators, wherein the diameter of a socket defined by the surface actuators can be made wider by use of the interstitial actuators.
Figure 8B:
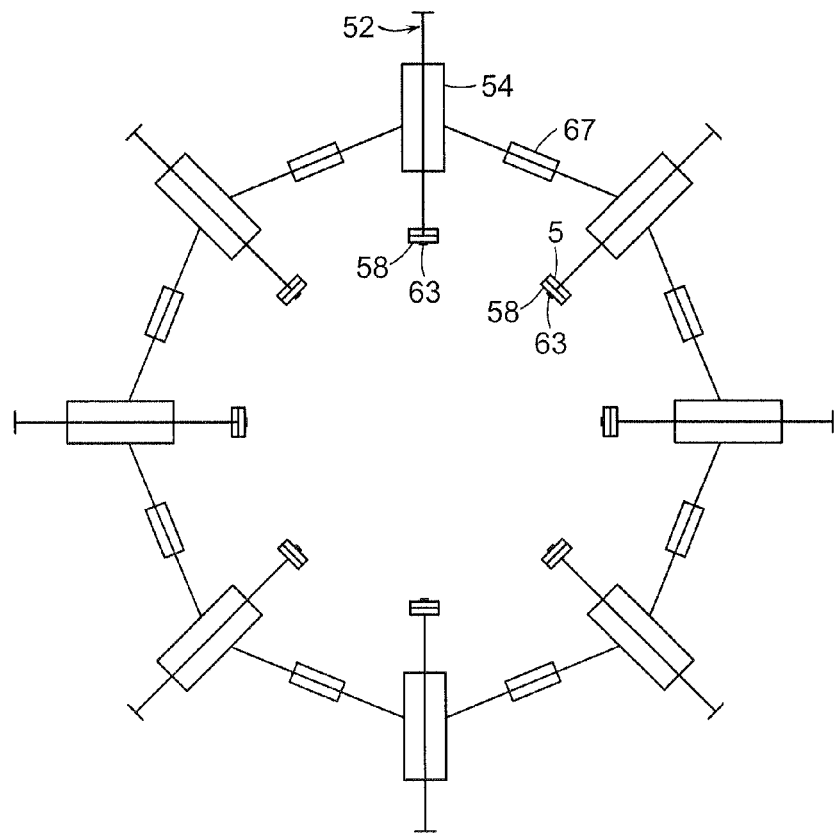
Figure 9:
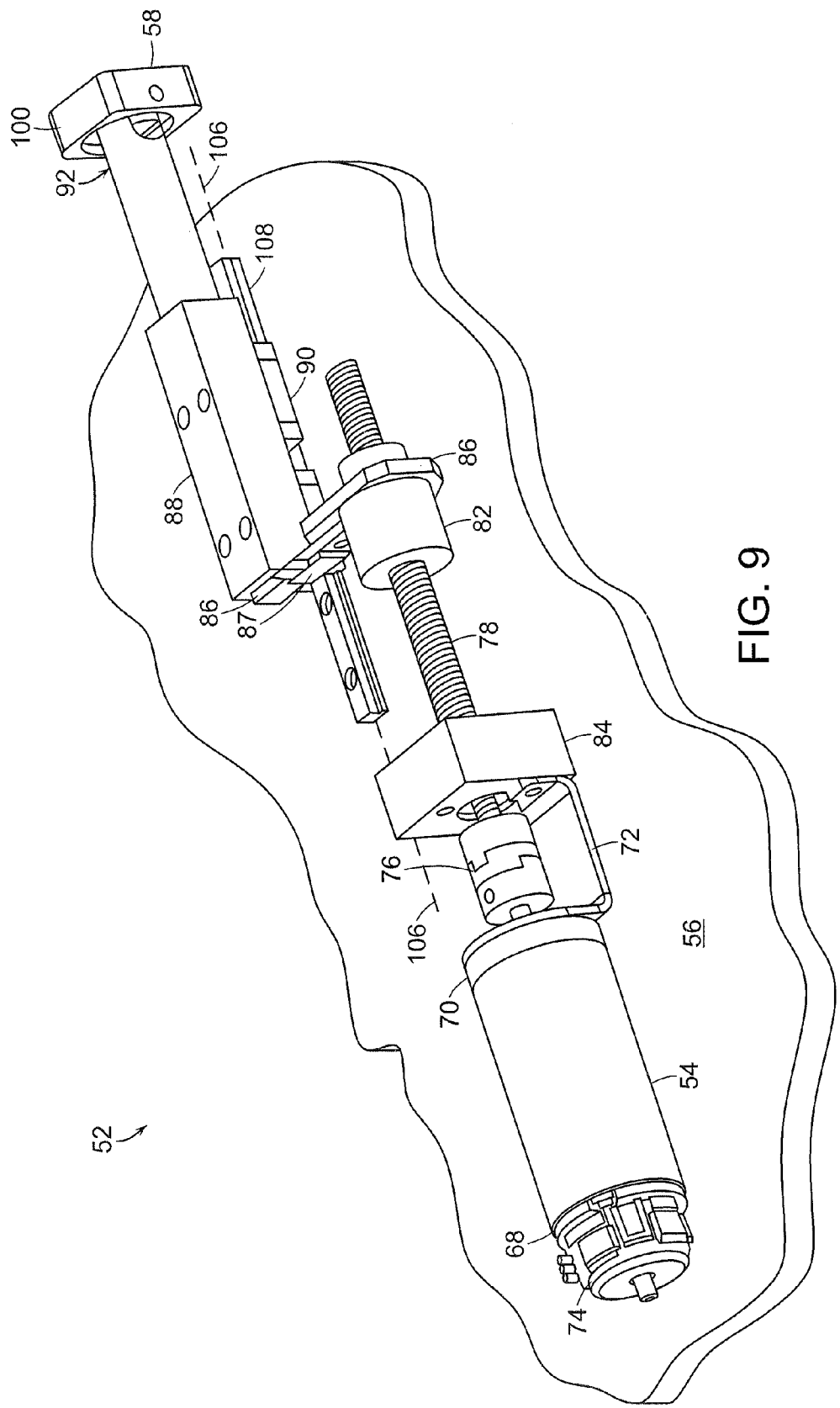
FIG. 9 is a perspective view of a surface actuator employable in the embodiment of the invention represented in FIG. 4.
Figure 10:
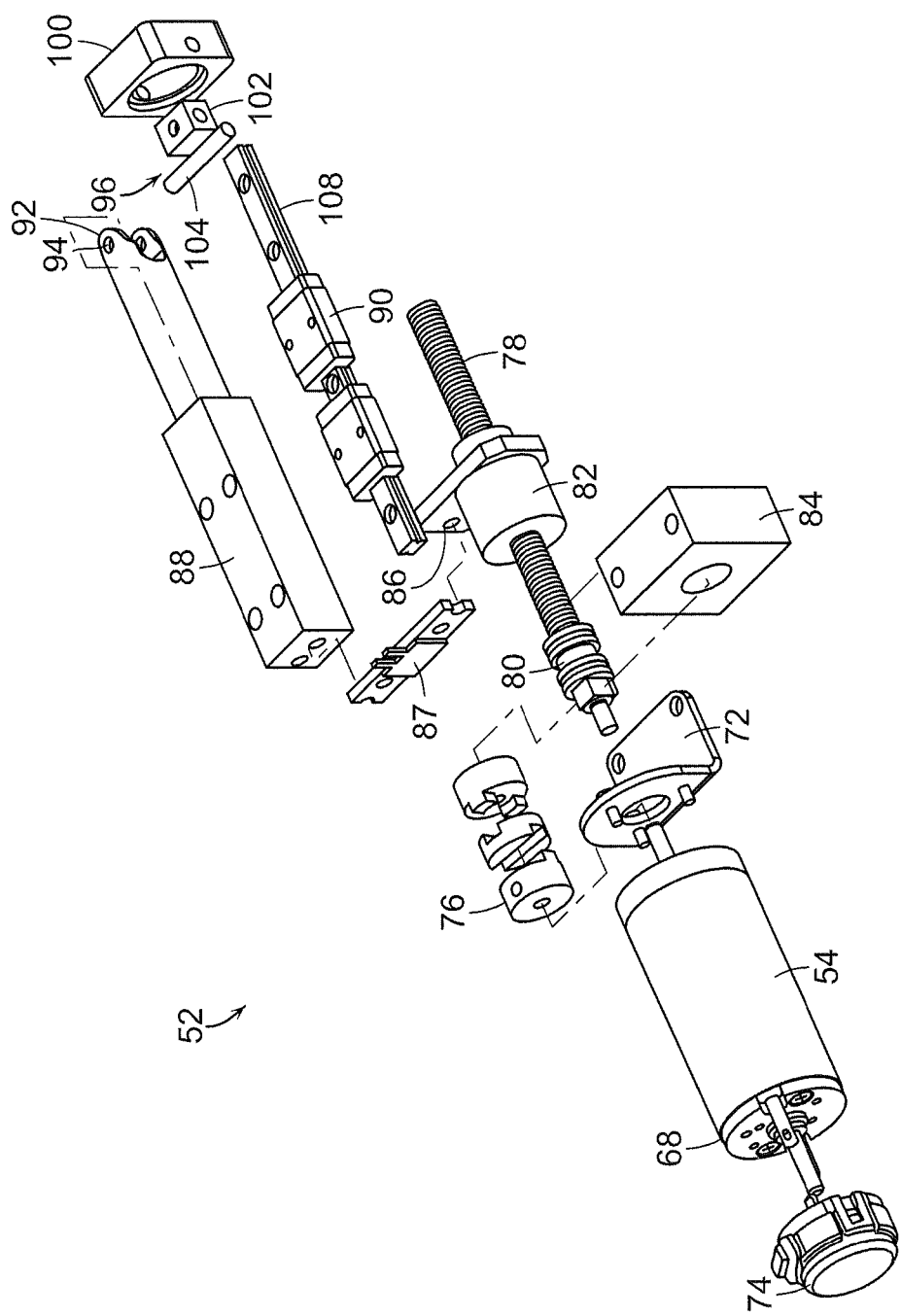
FIG. 10 is an exploded view of the surface actuator shown in FIG. 9.
Figure 11A:
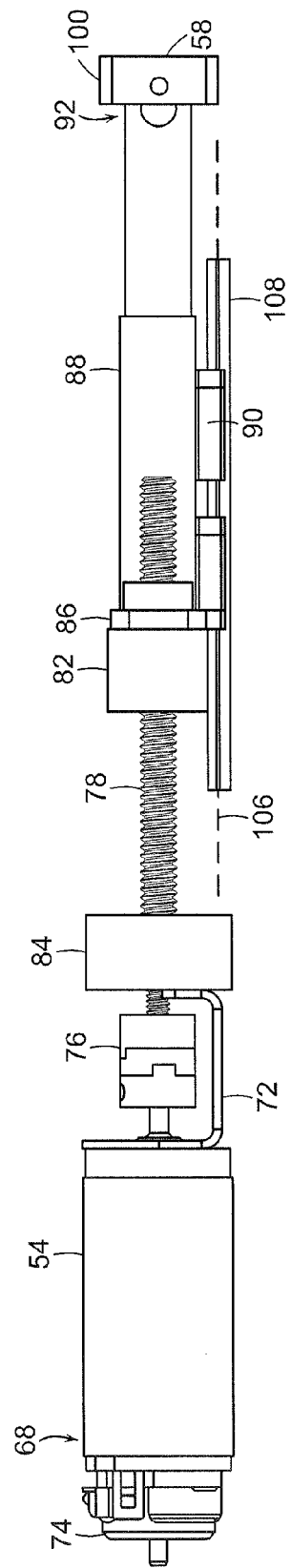
FIG. 11A is a side view of the surface actuator shown in FIG. 9.
Figure 11B:
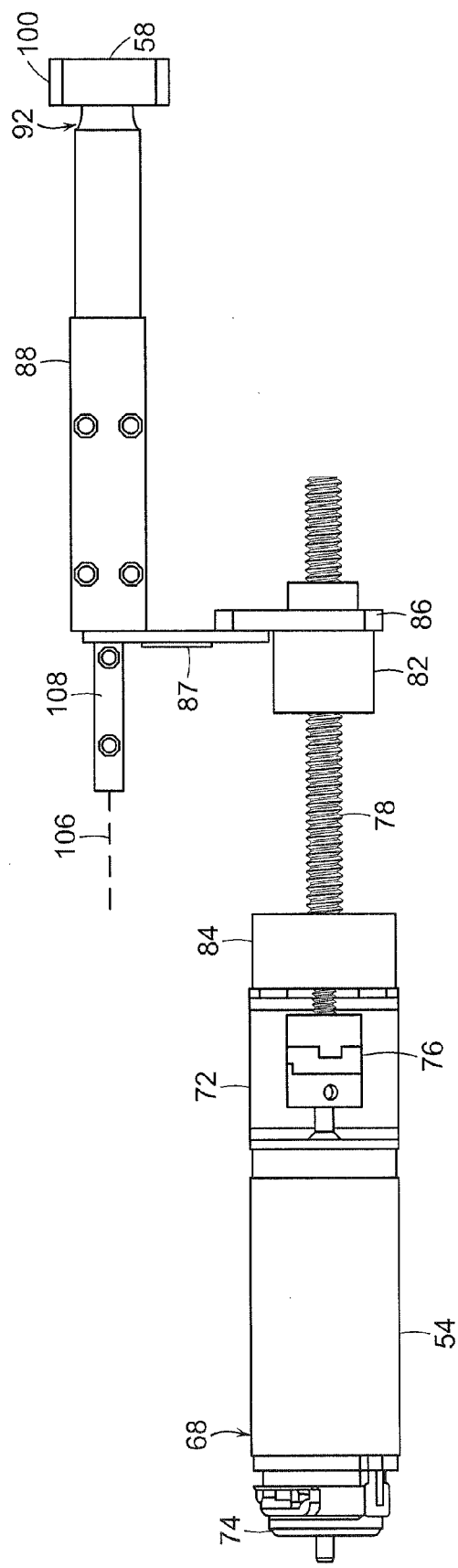
FIG. 11B is a plan view of the surface actuator shown in FIG. 9.

Another embodiment of the invention is shown in FIGS. 8A and 8B. As shown therein, surface actuators 52 are separated by interstitial actuators 67. Actuation of interstitial actuators 67 causes the distance between surface actuators 52 to change, thereby causing the distance between surfaces 58 to change, as shown in the transition between FIGS. 8A-8B. The diameter of a socket defined by surfaces 58 can thereby be manipulated beyond the range of motion of surfaces 58 of individual surface actuators 52 when an arrangement of surface actuators 52 are fixed in position relative to each other. Optionally surface actuators 52 can be linked to interstitial actuators 67 by a hinge at the intersection of surface actuators 52 and interstitial actuators 67 shown in FIGS. 8A and 8B.

One embodiment of surface actuator 52 suitable for use as an actuator of the physiological simulation measurement device of the invention is shown in FIGS. 9-11B. As shown therein, rotary motor 54 includes distal end 68 and proximal end 70, and is mounted at proximal end 70 to mounting bracket 72 that is, in turn, fixed to frame 56 (FIG. 4). Rotary encoder 74 at distal end 68 of rotary motor 54 and controls actuation of rotary motor 54. Shaft coupler 76 couples rotary motor 54 to ball screw 78 through bearing assembly 80. Bearing assembly 80 is fitted within bearing assembly block 84. Ball screw 78 is threaded onto ball nut 82 and is linked to linear thrust block 88 by coupling 86. Strain gauge force sensor 87 is located at coupling 86, and detects the amount of force applied to or by end-effector plate 100. Strain gauge force sensor 87 can be mounted on a single coupling or can span two coupling components, as is known in the art. Linear thrust block 88 is mounted to linear bearing 90. Linear bearing 90 is fixed directly or indirectly to frame 56. Distal end 92 of linear thrust block 88 is fitted onto vertical axis pivots 94 of two-axis joint 96. Two-axis joint 96 prevents interference between linear thrust block 88 and end-effector plate 100. Cube 102 is fitted over two-axis joint 96. End-effector plate 100 is fitted over horizontal pivot pin 104 of two-axis joint 96. End-effector plate 100 defines or supports surface 58 contacting a physiological feature of the subject for modeling or simulation.

Actuation of rotary motor 54 causes rotation of ball screw 78 and consequent longitudinal motion of linear thrust bearing 88 on linear bearing 90 along major longitudinal axis 106 of rail 108, thereby causing longitudinal motion of two-axis joint 96 on rail 108 and of end-effector plate 100 along major longitudinal axis 106 of rail 108. Optionally, a temperature sensor or another type of sensor can be placed at end-effector plates 100 in order to measure a physiological feature at the subject. End-effector plates 100 of surface actuators 52 can be contiguous, separated from each other, or overlap. In another embodiment, multiple surface actuators 52 can be linked to a single surface contacting end-effector plate 100 of each surface actuator 52. As described above, surface actuators 52 are linked to a processor or controller 11 (FIG. 1) by a suitable means, such as through circuit 110, shown in FIG. 7A, mounted on frame 56. Controller 11 and circuits 110 modulate surface actuators 52 and thereby modulate the position of surfaces at surface actuators 52 relative to the physiological feature of the subject to be measured or simulated. The processer may also, or alternatively, modulate frame actuators (FIG. 5) and interstitial actuators (FIGS. 7A-7D and 8). Surface actuators 52, through the processor, can modulate the position or force applied by each surface actuator to a surface of the subject, and can measure at least one of impedance, force and stiffness of tissue of the subject at the surface of each surface actuator. Further, modulation of the surface actuators can be conducted in response to sensors either at the surface actuators or remote from them, or both, such as sensors employed to detect body temperature, blood pressure, heart rate of the subject, or position of the sensors. The sensors can also be employed at the surface actuator to detect temperature of the surface of the subject at the end-effector plate or bladder surface of the surface actuator employed. Also, alternative types of actuators can be employed, such as actuators that include springs, such as linear or non-linear springs, as are known in the art.

Such modulation can be by virtue of the arrangement of surface actuators of the device of the invention, and by control of the invention, either manually or automatically, in response to feedback from sensors employed in combination with the array of surface actuators. Further, the invention allows independent control of the shape of a test socket or shape at the surface of the subject in real time. For example, a multi-surface system of the invention can be modulated to determine the ideal socket or surface shape and characteristics for a particular user with the aid of data generated in real time. The device can be capable of determining both the socket shape under load in real time due to physical interaction at the interface between the subject's tissue and the simulated wearable device surface of the invention. For example, shape and pressure data allow the stiffness and impedance of residual limb tissue to be calculated directly.

Typically, about two hundred individually-controlled surface actuators will be distributed across the surface of a patient to be fitted with an orthotic or prosthetic device. In the case of bladders, at least a portion of the surfaces of the bladders of the surface actuators are flexible. Surfaces in contact with a subject generally will move in a direction that is about normal to a surface of the subject, while restricting tangential movement. The number of surface actuators per actuation surface can range, for example, between about 0.25 and about 3 surface actuators per actuation surface. Feedback from sensors at the surface actuators can be employed to form a three-dimensional image of the surface with which the actuators are in direct or indirect contact. Further, changes in the image can be portrayed in real-time and can reflect not only changes in position of the surface, but distribution of forces at the points of the surface and distribution of temperature at different points of the surface.

EQUIVALENTS

While this invention has been particularly shown and described with references to example embodiments thereof, it will be understood by those skilled in the art that various changes in form and details may be made therein without departing from the scope of the invention encompassed by the appended claims.

The relevant teachings of all references cited are incorporated herein by reference in their entirety.

What is claimed is:

1. A physiological measurement device or wearable device interface simulator, comprising:
   a) a frame;
   b) a plurality of surfaces distributed within the frame; and
   c) for each surface, a surface actuator linking the surface to the frame, the surface actuators modulating independently
      i) the forces applied by the surfaces to a subject, and
      ii) the positions of the surfaces relative to each other and relative to the subject,
      thereby measuring a physiological feature of the subject or simulating a wearable device interface.

2. The device or simulator of claim 1, further including a sensor at at least a portion of the surfaces, whereby feedback from the sensor can be employed to modulate the relative positions of the surfaces.

3. The device or simulator of claim 2, wherein the sensor is a pressure sensor.

4. The device or simulator of claim 2, wherein the sensor is a temperature sensor.

5. The device or simulator of claim 2, wherein the sensor is a position sensor.

6. The device or simulator of claim 2, wherein the modulation of force imparted by at least one of the surfaces is in response to at least one of a) a force applied to the sensor by the subject, and b) a change in position of at least a portion of the surfaces relative to each other, the frame, or relative to the subject.

7. The device or simulator of claim 1, further including at least one frame actuator, wherein position of the frame relative to the subject can be modulated by activating the frame actuator.

8. The device or simulator of claim 1, further including at least one interstitial actuator linking the surface actuators, wherein positions of the surface actuators relative to each other are modulated by activation of the interstitial actuator.

9. The device or simulator of claim 1, wherein the position of the frame is configured to be modulated relative to a physiologic skeletal feature of the subject proximate to the physiological feature of the subject to be measured or simulated.

10. The device or simulator of claim 1, wherein the actuator is configured to modulate the resistive force of the subject.

11. The device or simulator of claim 1, wherein the modulation of the positions of the surfaces is in response to a force upon at least a portion of the surfaces by the subject.

12. The device or simulator of claim 1, wherein the device is further configured to modulate the force imparted by at least a portion of the surfaces on the subject.

13. The device or simulator of claim 12, wherein the modulation of force is at least one member selected from the group consisting of stiffness, damping and impedance.

14. The device or simulator of claim 1, further including a controller that relates the force and positions of each surface to each surface actuator.

15. The device or simulator of claim 14, wherein the controller modulates at least one of the relative positions of the surfaces and the resistive forces applied by the surfaces on the subject.

16. The device or simulator of claim 15, wherein the modulation is of a combination of the relative positions of the surfaces, and the resistive forces applied by the surfaces on the subject.

17. The device or simulator of claim 16, wherein the controller simulates the interface between the surfaces and the physiological subject contacting the surfaces by mapping at least one of the position, force and temperature measured by sensors contacting the subject.

18. The device or simulator of claim 1, wherein the actuator includes a bladder supporting each surface and a potentiometer, wherein the bladder is filled with a gas or an incompressible fluid, and wherein the force imparted by each surface is modulated by modulating the volume of gas or incompressible fluid within the bladder.

19. The device or simulator of claim 1, wherein the actuator includes a motor that is linked to the surface by a screw drive, and at least one of a) a position sensor at the motor to detect the position of the surface, b) a force sensor at the surface or linked to the surface, and c) a temperature sensor at the surface.

20. The device or simulator of claim 1, wherein the surfaces are arrayed in a plane, wherein each surface is normal to the plane, and the surfaces collectively define an opening into which the subject can be placed.

21. The device or simulator of claim 1, wherein the surfaces are arranged three-dimensionally and define a shape such that the surfaces make contact with a subject's body.

22. A method for measuring a physiological feature of a subject or simulating an interface of a wearable device, comprising the steps of:
   a) placing a plurality of surfaces against a subject, at least a portion of the surfaces each being linked to a frame by a surface actuator; and
   b) modulating independently of each other
      i) the forces applied by the surfaces to the subject, and
      ii) the positions of the surfaces relative to each other and relative to the subject, to thereby measure a physiological feature of the subject or simulate an interface of a wearable device.

23. The method of claim 22, wherein the surfaces are arrayed in a plane, wherein each surface is normal to the plane, and the surfaces collectively define an opening into which the subject can be placed.

24. The method of claim 22, wherein the surfaces are arranged three-dimensionally and define a shape such that the surfaces make contact with a subject's body.

25. The method of claim 22, wherein the support includes a frame actuator, and further including the step of activating the frame actuator to modulate the position of the frame relative to the subject.

26. The method of claim 22, wherein the support includes at least one interstitial actuator linking the surface actuators, and further including the step of actuating at least one interstitial actuator to thereby modulate the positions of the surface actuators relative to each other.

27. The method of claim 22, wherein at least a portion of the surfaces each include a sensor, and further including the step of independently modulating the relative positions of, or forces applied by, the surfaces in response to feedback from the sensors.

28. The method of claim 27, wherein the sensor is a pressure sensor.

29. The method of claim 27, wherein the sensor is a thermometer.

30. The method of claim 27, wherein the sensor is a position sensor.

31. The method of claim 27, wherein the modulation includes activating at least a portion of the surface actuators.

32. The method of claim 27, wherein the modulation includes activating at least one frame actuator changing the position of the frame relative to the subject.

33. The method of claim 27, wherein the modulation includes activating at least one interstitial actuator linking surface actuators, thereby modulating the positions of the surface actuators relative to each other.

34. The method of claim 22, further including the step of modulating the position of the frame relative to a physiological skeletal feature of the subject.

\* \* \* \* \*